(12) United States Patent
Højlund et al.

(10) Patent No.: US 7,470,542 B2
(45) Date of Patent: Dec. 30, 2008

(54) PROTEINS IN TYPE 2 DIABETES

(75) Inventors: Kurt Højlund, Odense M (DK); Stephen J. Fey, Arhus C (DK); Peter Mose Larsen, Odense S (DK); Henning Beck-Nielsen, Odense M (DK); Krzysztof Wrzesinski, Odense S (DK)

(73) Assignee: Pride Proteomics A/S, Odense M (DK)

( * ) Notice: Subject to any disclaimer, the term of this patent is extended or adjusted under 35 U.S.C. 154(b) by 335 days.

(21) Appl. No.: 10/488,460

(22) PCT Filed: Sep. 5, 2002

(86) PCT No.: PCT/DK02/00576

§ 371 (c)(1), (2), (4) Date: Oct. 29, 2004

(87) PCT Pub. No.: WO03/020963

PCT Pub. Date: Mar. 13, 2003

(65) Prior Publication Data

US 2006/0166299 A1 Jul. 27, 2006

(30) Foreign Application Priority Data

Sep. 5, 2001 (DK) ............................... 2001 01298

(51) Int. Cl.
*G01N 33/48* (2006.01)
*G01N 33/00* (2006.01)
*C12Q 1/48* (2006.01)
*C12Q 1/50* (2006.01)

(52) U.S. Cl. ............................ 436/63; 436/86; 435/15; 435/17

(58) Field of Classification Search ............................ None
See application file for complete search history.

(56) References Cited

U.S. PATENT DOCUMENTS 5,786,150 A 7/1998 Hillman et al.
6,140,067 A 10/2000 Anderson et al.

FOREIGN PATENT DOCUMENTS

| WO | WO 98/17826 A | 4/1998 |
|---|---|---|
| WO | WO 98/20124 A | 5/1998 |
| WO | WO 99/36526 A1 | 7/1999 |
| WO | WO-00/04037 | 1/2000 |
| WO | WO 00/66762 A2 | 11/2000 |
| WO | WO 00/66782 A2 | 11/2000 |
| WO | WO 01/34833 A | 5/2001 |

OTHER PUBLICATIONS

Capuano et al. Oxidative Phosphorylation and F0F1 ATP Synthase Activity of Human Hepatocellular Carcinoma; Biochemistry and Molecular Biology International, vol. 38, No. 5 (1996) pp. 1013-1022.*

Mayfield, J. Diagnosis and Classification of Diabetes Mellitus: New Criteria; American Family Physician, vol. 58, No. 6 (1998).*

Seffernick et al. Melamine Deaminase and Atrazine Chlorohydrolase: 98% Identical But Functionally Different; Journal of Bacteriology, vol. 183, No. 8 (2001) pp. 2405-2410.*

Kelley, D.E. et al., "Fuel selection in human skeletal muscle in insulin resistance. A reexamination," Diabetes 49, 677-683 (2000).

Gebhart, S. et al., "Insulin resistance associated with maternally inherited diabetes and deafness," Metabolism. 45, 526-531 (1996).

Wallace, D.C., "Mitochrondrial diseases in man and mouse," Science 283, 1482-1488 (1999).

Pandey, P. et al., "Proteomics to study genes and genomes," Nature 405, 837-846 (2000).

Hickson, R.C. et al., "Skeletal muscle enzyme alterations after sprint and endurance training," Appl. Physiol. 40, 868-871 (1976).

Lillioja, S. et al., "Skeletal muscle capillary density, and fiber type are possible determinants of in vivo resistance in man," J. Gun. Invest. 80, 415-424 (1987).

Pearl, H.P. et al., "Structure and in vivo function of Hsp90," Curr. Opin. Strct. Biol. 10, 46-51 (2000).

Nishizawa, J. et al., "Reactive oxygen species play an important role in the activation of heat shock factor 1 in ischemic-reperfused heart," Circulation 99, 934-941 (2000).

Nishikawa, T. et al., "Normalizing mitochondrial superoxide production blocks three pathways of hyperglycaemic damage," Nautre 404, 787-790 (2000).

Sato, S. et al., "Modulation of Akt kinase activity by binding to Hsp90," Proc. Natl. Acad. Sci. USA 97, 10832-10837 (2000).

Garcia-Cardena, G. et al., "Dynamic activation of endothelial nitric oxide synthase by Hsp90," Nature 392, 821-824 (1998).

Fryer, L.G.D. et al., "Activation of glucose transport by AMP-activated protein kinase via stimulation of nitric oxide synthase," Diabetes 49, 1978-1985 (2000).

Poetter, K. et al., "Mutations in either essential or regulatory light chains of myosin are associated with a rare myopathy in human heart and skeletal muscle," Nature Genetics 13, 63-69 (1996).

Apple, F. S., "Tissue specificity of cardiac troponin I, cardiac troponin T and creatine kinase-MB," Clin. Chem. Acta. 284, 151-159 (1999).

Apple, F.S. et al., "CK and LD isoenzymes in human single muscle fibres in trained athletes," J. Appl. Physiol. 66, 2717-2720 (1989).

Wallimann, T. et al., "Some new aspects of creatine Kinease (CK): compartmentation, structure, function and regulation for cellular and mitochondrial bioenergetics and physiology," Biofactors 8, 299-234 (1998).

(Continued)

*Primary Examiner*—Jon P Weber
*Assistant Examiner*—Paul C. Martin
(74) *Attorney, Agent, or Firm*—Birch, Stewart, Kolasch & Birch, LLP

(57) ABSTRACT

The present invention relates to the use of naturally occurring compounds and derivatives thereof as markers for predisposition of diabetes related diseases. The invention also relates to a pharmaceutical composition for treatment of the diabetes related diseases.

1 Claim, 8 Drawing Sheets

OTHER PUBLICATIONS

Winder, W.W. et al., "AMP-activated protein kinase, a metobolic master switch: possible roles in Type 2 diabetes," Am. J. Physiol. Endocrinol. Metab. 277, E1-E10 (1999).

Boyer, P.D. "Catalytic site forms and controls in ATP synthase catalysis," Biochim. Biophys. Acta. 1458, 252-262 (2000).

Groth, G. et al., "Characterization of a phosphate binding domain on the ∝-subunit of chloroplast ATP synthase using the photoaffinity phosphate analogue 4-azido-2-nitrophenyl phosphate," Biochemistry 39, 13781-13787 (2000).

Wu, Z. et al., "Mechanism cntrolling mitochondrial biogenesis and respiration through the thermogenic coactivator PGC-I," Cell 98, 115-124 (1999).

Gonzalez, B. et al., "Stress proteins of 70 kDa in chronically exercised skeletal muscle," Pflugers Arch—Eur. J. Physiol. 440, 42-49 (2000).

Boss,O. et al., "Uncoupling proteins 2 and 3. Potential regulators of mitochondrial energy metabolism," Diabetes 49, 143-156 (2000).

Shrauwen, P. et al., "The effect of weight reduction on skeletal muscle UCP2 and UCP3 mRNA expression and UCP3 protein content in Type II diabetic subjects," Diabetologia 43, 1408-1416 (2000).

Bao, S. et al., "Expression of mRNAs encoding uncoupling proteins in human skeletal muscle. Effects of obesity and diabetes," Diabetes 47, 1935-1940 (199*).

Hojlund, K. et al., "Reference intervals for glucose, n-cell polypeptides, and counterregulatory factors during prolonged fasting," Am. J. Physiol. Endocrinol. Metab. 280, E50-E58 (2001).

Fey, S. J. et al., "Proteome analysis of *Saccharmomyces cerevisiae*: a methodological outline," Electrophoresis 8, 1361-1372 (1997).

Jensen, O. N. et al., "Mass spectrometric identification and microcharacterization of proteins from electrophoretic gels: strategies and applications," Proteins 2 74-89 (1998).

Hemmer, W., Skarli, M. Perriard, J. C. & Wallimann, T. (19993) FEBS Letters 327, 35-40.

Manning, D. R. & Stull, S. (1982) Am. J. Physiol. 242, C234-241.

Menz, R.I., Walker, J.E. & Leslie, A. G. W. (2001) Cell 106, 331-341.

Vincent, D. et al., "Aleterations in skeletal muscle gene expression of obiob Mice by mRNA differential display," Diabetes 47, 1451-1458 (Sep. 1998).

Kagawa, Y. et al., "Regulation of energy metabolism in human cells in aging and diabetes: F0f$_1$, mtDNA, UCP, and ROS," Biochemical and Biophysical Research Communications 266, 662-676 (1999).

Database EMBL [Online] created Nov. 26, 1990, "The human ATP synthase beta subunit gene: sequence analys assignment, and differential expression,"retrieved from EBI accession No. M27132, the whole document.

Beck-Nielsen, H., "Mechanisms of insulin resistance in non-oxidative glucose metabolism: The role of glycogen synthase," J. Basic Clin. Physiol. Pharmacol. 9, 255-279 (1998), (Abstract only).

* cited by examiner

ATP synthase β-subunit (SEQ ID NO: 2)

```
  1 ------------------------------------------AQTSPSPKAGAAT
 61 GRIVAVIGAVVDVQFDEGLPPILNALEVQGRETRLVLEVAQHLGESTVRTIAMDGTEGLV
121 RGQKVLDSGAPIKIPVGPETLGRIMNVIGEPIDERGPIKTKQFAPIHAEAPEFMEMSVEQ
181 EILVTGIKVVDLLAPYAKGGKIGL[FGGAGVGKT]VLIMELINNVAKAHGGYSVFAGVGERT
241 REGNDLYHEMIESGVINLKDATSKVALVYGQMNEPPGARARVALTGLTVAEYFRDQEGQD
301 VLLFIDNIFRFTQAGSEVSALLGRIPSAVGYQPTLATDMGTMQERITTTKKGSITSVQAI
361 YVPADDLTDPAPATTFAHLDATTVLSRAIAELGIYPAVDPLDSTSRIMDPNIVGSEHYDV
421 ARGVQKILQDYKSLQDIIAILGMDELSEEDKLTVSRARKIQRFLSQPFQVAEVFTGHMGK
481 LVPLKETIKGFQQILAGEYDHLPEQAFYMVGPIEEAVAKADKLAEEHSS
```

Prior Art

Fig. 2C

SEQUENCE LISTING

```
<160> NUMBER OF SEQ ID NOS: 2

<210> SEQ ID NO 1
<211> LENGTH: 13
<212> TYPE: PRT
<213> ORGANISM: Homo sapien
<220> FEATURE:
<221> NAME/KEY: misc_feature
<222> LOCATION: (1)..(13)
<223> OTHER INFORMATION: Amino acids 213-222 of ATP Synthase beta
      subunit

<400> SEQUENCE: 1

Thr Val Leu Ile Met Glu Leu Ile Asn Asn Val Ala Lys
1               5                   10

<210> SEQ ID NO 2
<211> LENGTH: 482
<212> TYPE: PRT
<213> ORGANISM: Homo sapien
<220> FEATURE:
<221> NAME/KEY: misc_feature
<222> LOCATION: (1)..(482)
<223> OTHER INFORMATION: Amino acid sequence of ATP Synthase beta
      subunit

<400> SEQUENCE: 2

Ala Gln Thr Ser Pro Ser Pro Lys Ala Gly Ala Ala Thr Gly Arg Ile
1               5                   10                  15

Val Ala Val Ile Gly Ala Val Val Asp Val Gln Phe Asp Glu Gly Leu
            20                  25                  30

Pro Pro Ile Leu Asn Ala Leu Glu Val Gln Gly Arg Glu Thr Arg Leu
        35                  40                  45

Val Leu Glu Val Ala Gln His Leu Gly Glu Ser Thr Val Arg Thr Ile
    50                  55                  60

Ala Met Asp Gly Thr Glu Gly Leu Val Arg Gly Gln Lys Val Leu Asp
65                  70                  75                  80

Ser Gly Ala Pro Ile Lys Ile Pro Val Gly Pro Glu Thr Leu Gly Arg
                85                  90                  95

Ile Met Asn Val Ile Gly Glu Pro Ile Asp Glu Arg Gly Pro Ile Lys
            100                 105                 110

Thr Lys Gln Phe Ala Pro Ile His Ala Glu Ala Pro Glu Phe Met Glu
        115                 120                 125
```

```
Met Ser Val Glu Gln Glu Ile Leu Val Thr Gly Ile Lys Val Val Asp
    130                 135                 140
Leu Leu Ala Pro Tyr Ala Lys Gly Gly Lys Ile Gly Leu Phe Gly Gly
145                 150                 155                 160
Ala Gly Val Gly Lys Thr Val Lys Ile Met Glu Leu Ile Asn Asn Val
                165                 170                 175
Ala Lys Ala His Gly Gly Tyr Ser Val Phe Ala Gly Val Gly Glu Arg
            180                 185                 190
Thr Arg Glu Gly Asn Asp Leu Tyr His Glu Met Ile Glu Ser Gly Val
        195                 200                 205
Ile Asn Leu Lys Asp Ala Thr Ser Lys Val Ala Leu Val Tyr Gly Gln
    210                 215                 220
Met Asn Glu Pro Pro Gly Ala Arg Ala Arg Val Ala Leu Thr Gly Leu
225                 230                 235                 240
Thr Val Ala Glu Tyr Phe Arg Asp Gln Glu Gly Gln Asp Val Leu Leu
                245                 250                 255
Phe Ile Asp Asn Ile Phe Arg Phe Thr Gln Ala Gly Ser Glu Val Ser
            260                 265                 270
Ala Leu Leu Gly Arg Ile Pro Ser Ala Val Gly Tyr Gln Pro Thr Leu
        275                 280                 285
Ala Thr Asp Met Gly Thr Met Gln Glu Arg Ile Thr Thr Thr Lys Lys
    290                 295                 300
Gly Ser Ile Thr Ser Val Gln Ala Ile Tyr Val Pro Ala Asp Asp Leu
305                 310                 315                 320
Thr Asp Pro Ala Pro Ala Thr Thr Phe Ala His Leu Asp Ala Thr Thr
                325                 330                 335
Val Leu Ser Arg Ala Ile Ala Glu Leu Gly Ile Tyr Pro Ala Val Asp
            340                 345                 350
Pro Leu Asp Ser Thr Ser Arg Ile Met Asp Pro Asn Ile Val Gly Ser
        355                 360                 365
Glu His Tyr Asp Val Ala Arg Gly Val Gln Lys Ile Leu Gln Asp Tyr
    370                 375                 380
Lys Ser Leu Gln Asp Ile Ile Ala Ile Leu Gly Met Asp Glu Leu Ser
385                 390                 395                 400
Glu Glu Asp Lys Leu Thr Val Ser Arg Ala Arg Lys Ile Gln Arg Phe
                405                 410                 415
Leu Ser Gln Pro Phe Gln Val Ala Glu Val Phe Thr Gly His Met Gly
            420                 425                 430
Lys Leu Val Pro Leu Lys Glu Thr Ile Lys Gly Phe Gln Gln Ile Leu
        435                 440                 445
Ala Gly Glu Tyr Asp His Leu Pro Glu Gln Ala Phe Tyr Met Val Gly
    450                 455                 460
Pro Ile Glu Glu Ala Val Ala Lys Ala Asp Lys Leu Ala Glu Glu His
465                 470                 475                 480
Ser Ser
```

PROTEINS IN TYPE 2 DIABETES

FIELD OF INVENTION

The present invention relates to a method for diagnosis or prediction of predisposition of diabetes related diseases and pharmaceutical compositions for treatment of diabetes-related diseases.

BACKGROUND OF THE INVENTION

Diabetes is sub-divided on clinical grounds into insulin-dependent and non-insulin dependent diabetes mellitus (IDDM (type 1) and NIDDM (type 2) respectively). The two forms of the disease are distinguished by a number of features.

In type 1 diabetes there is profound insulin deficiency such that even the low levels of insulin which would normally prevent lipolysis and cytogenesis cannot be sustained. Type 1 patients therefore generally show high levels of glucose and low levels of insulin. As the disease progresses, the pancreatic islets are damaged or destroyed, and less and less insulin can be produced.

Type 2 diabetes is a common and complex disorder, which results from a combination of defects in insulin secretion and impaired insulin sensitivity (insulin resistance) in peripheral tissues, e.g. in skeletal muscle (1). Type 2 diabetes is characterized by hyperglycaemia in both the fasted and fed states, variable degrees of hyperinsulinaemia and obesity. Despite intensive investigation of proteins in insulin signaling pathways in the past decade, the primary cellular cause remains uncertain. Recent reports of reduced oxidative enzyme activity in type 2 diabetic muscle (2), and of mitochondrial DNA mutations causing type 2 diabetes through impairment of oxidative phosphorylation (3,4), add to the molecular complexity of this disease.

Current therapy includes diet, sulphonylurea to enhance insulin secretion, insulin itself, and biguanides to reduce insulin resistance. There is a need for new antidiabetic agents, since biguanides are quite toxic while sulphonylurea is ineffective in patients with severely impaired islet cell function, and after 10 years of treatment, 50% of patients will have become resistant.

A number of strategies have been employed in order to determining the predisposition of diabetes. In WO 00/66762, to which reference is made, it is described that specific mutations in the mitochondrial gene ATP synthase 8/6 sequence can be related to diabetes.

Further, WO 00/66782 and WO 98/17826 describe a method for diagnosing diabetes by finding mutations in an ATP synthase gene.

Though several strategies for determining the risk of developing diabetes have been suggested, no strategy has proven successful. The present invention therefore fulfils the long-felt need for a method for determining the risk of developing diabetes.

SUMMARY OF THE INVENTION

The present inventors have invented a method for diagnosing and determining the predisposition of at least one disease relating to diabetes by measuring the level of a protein in a sample. The invention is based on the finding that fifteen proteins surprisingly were either down- or up-regulated in type 2-diabetes. Eleven of these proteins (markers for type 2 diabetes) were positively identified by mass spectrometry. The observed changes in the expression of these eleven proteins are consistent with increased cellular stress and perturbations in skeletal muscle mitochondrial metabolism in insulin resistant subjects (2). Most of the proteins identified were either phosphoproteins or proteins involved in phosphate metabolism in the cell. Most interestingly, the present inventors demonstrated that ATP synthase beta-subunit is phosphorylated, and found the expression of a beta-subunit phospho-isoform to be reduced and to correlate inversely with fasting plasma glucose levels in diabetic muscle. These data indicate a role for phosphorylation of ATP synthase beta-subunit in the regulation of ATP synthesis, and that alterations in the regulation of this protein and cellular stress proteins may contribute to pathogenesis of type 2 diabetes.

With regard to a method of treating diabetes, a single protein may be targeted for therapy or a grouping of proteins may be targeted. The level of expression of these targeted proteins may be altered (e.g. increased or decreased) or the proteins themselves may be interfered with in a method of preventing or delaying the onset of a diabetes related disease in a human according to the invention. This may be accomplished by administering e.g. a marker protein, a nucleotide sequence (or complementary sequence or part thereof) coding for a marker protein, an antibody for a marker protein, a nucleic acid fragment capable of binding to a marker protein, and/or a compound capable of binding to a marker protein to said human. Compounds which affect the transcription of a marker or effect the post-translational modification of a marker, and especially compounds which affect the activity (phosphorylation status) of a marker protein, would also be obvious drug candidates.

DETAILED DISCLOSURE OF THE INVENTION

The present invention relates to a substantially pure polypeptide, which comprises at least one amino acid sequence selected from the group consisting of:
  (a) ATP synthase beta subunit or phosphorylated ATP synthase beta subunit isoforms;
  (b) phosphoglucomutase 1;
  (c) heat shock protein 90 beta;
  (d) creatine kinase B subunit;
  (e) myosin regulatory light chain 2;
  (f) collagen alpha1 (VI) chain;
  (g) 78 kDa glucose-regulated protein;
  (h) a marker protein defined by the characteristics disclosed in table 3 (match nos: 199, 303, 391, or 511);
  (i) an analogue having preferably at least 70% (such as at least 80%, at least 90%, at least 95%) homology with any one of the polypeptides in (a), (b), (c), (d), (e), (f), (g) or (h) or a part thereof; and
  (j) a derivative, precursor, analogue or modification of an amino acid sequence in (a), (b), (c), (d), (e), (f), (g), (h) or (i).

ATP synthase beta subunit is a nuclear encoded protein, and the subunit is placed in the catalytic part of the ATP synthase enzyme (in the F1 part), in contrast to the ATP synthase 6/8 subunits which are mitochondrial encoded proteins, and are placed in the catalytic inactive membrane spanning part of the ATP synthase enzyme (in the F0 part).

The polypeptides, including their phosphorylated isoforms, can be used as a medication, e.g. for treatment of at least one diabetes-related disease, preferably type 2 diabetes.

The invention further relates to a pharmaceutical composition for treatment of at least one diabetes-related disease, preferably type 2 diabetes, which comprises at least one polypeptide according to the invention or a mimetic or an antimimetic thereof. Other pharmaceutical compositions according to the invention are such compositions which comprise:

(a) at least one substance which is capable of regulating the expression of a nucleic acid fragment coding for at least a part of a polypeptide according to the invention; and/or
(b) at least one said polypeptide; and/or
(c) at least one antibody raised against said polypeptide or its modification product; and/or
(d) at least one nucleic acid fragment capable of hybridizing to a nucleotide sequence including its regulatory elements encoding said polypeptide or to the complementary strand; and/or
(e) at least one compound, e.g. a nucleic acid fragment, capable of binding to said polypeptide; and/or
(f) at least one compound capable of modifying the protein form associated with the disease so that its relative expression, activity and/or concentration is changed towards that seen in healthy persons; and/or
(g) at least one compound capable of marking (e.g. with ubiquinone) at least one of said proteins which protein is expressed at too high relative levels in the disease for more rapid turnover or degradation; and/or
(h) at least one compound capable of marking at least one of said proteins which protein is expressed at too low relative levels for slower turnover or degradation; and/or
(i) an aptamer which binds to said protein or the site at which said protein binds; and/or
(j) an aptamer which binds preferably to either the binding site or the active site of said protein.

The pharmaceutical composition comprises at least one active compound, e.g. 1, 2, 3, 4, 5, 6, 7, 8, 9, 10 or more different compounds.

In another embodiment, the invention relates to a method of treating a diabetes-related disease, preventing said disease and/or delaying the onset of said disease in a human, which method comprising administering at least one compound chosen from the group consisting of:

(a) a polypeptide according to the invention;
(b) a nucleotide sequence coding for the polypeptide in (a);
(c) an antibody able to bind the polypeptide in (a);
(d) a nucleic acid fragment capable of hybridizing to a nucleic acid encoding at least a part of the polypeptide in (a) or the complementary strand to said nucleic acid, including its regulatory elements;
(e) a compound capable of binding to the polypeptide in (a);
(f) a compound capable of up- or down regulating the expression, activity and/or concentration of at least one polypeptide according to the invention;
(g) a compound capable of modifying the protein form associated with the disease so that its relative expression, activity and/or concentration is changed towards that seen in healthy persons;
(h) a compound capable of marking (e.g. with ubiquinone) at least one of said proteins which protein is expressed at too high relative levels in the disease for more rapid turnover or degradation; and
(i) a compound capable of marking at least one of said proteins which protein is expressed at too low relative levels for slower turnover or degradation;

to said human. The treatment should preferably have the effect of returning the level of the marker proteins back to the levels seen in healthy controls.

In a presently preferred embodiment, the phosphorylation of ATP synthase beta subunit is regulated, e.g. up-regulated, as the phosphorylation of ATP synthase beta subunit is believed to alter the function of the enzyme. The phosphorylation can be regulated by regulating the kinases or phosphatases which phosphorylate or dephosphorylate the ATP syntase beta subunit.

Expression of ATP synthase beta subunit is regulated by a transcriptional "co-activator of PPARγ" called PPARγ co-activator-1 (PGC-1). This activator can thus be used as a means for up-regulating ATP synthase beta subunit.

In another embodiment, the invention relates to a method for diagnosing or determining the predisposition of at least one disease relating to diabetes, preferably type 2 diabetes, in a human, the method comprises determining the presence, activity, concentration and/or level of expression of at least one marker protein in a biological sample from the human, wherein the marker protein is selected from the group consisting of:

(a) ATP synthase beta subunit or phosphorylated ATP synthase beta subunit isoforms;
(b) phosphoglucomutase 1;
(c) heat shock protein 90 beta;
(d) creatine kinase B subunit;
(e) myosin regulatory light chain 2;
(f) collagen alpha1 (VI) chain;
(g) 78 kDa glucose-regulated protein;
(h) a marker protein defined by the characteristics disclosed in table 3 (match nos: 199, 303, 391, or 511);
(i) an analogue having preferably at least 70% homology with any one of the polypeptides in (a), (b), (c), (d), (e), (f), (g) or (h) or a part thereof; and
(j) a derivative, precursor, analogue or modification of an amino acid sequence in (a) to (i); and optionally comparing the presence, activity, concentration and/or level of expression of said protein with the presence, activity, concentration and/or level of expression of said protein in biological sample from at least one normal human (i.e. not suffering from the disease in question).

The method preferably comprises:

(A) determining the increased expression, modification, activity and/or concentration, in a biological sample from the human, of at least one marker protein selected from the group consisting of:
  (a) phosphoglucomutase 1;
  (b) heat shock protein 90 beta;
  (c) myosin regulatory light chain 2 up-regulated isoform;
  (d) collagen alpha1 (VI) chain;
  (e) 78 kDa glucose-regulated protein;
  (f) a marker protein defined by the characteristics disclosed in table 3 (match nos: 303, or 511);
  (g) an analogue having preferably at least 70% homology with any one of the polypeptides in (a), (b), (c), (d), (e) or (f) or a part thereof; and
  (h) a derivative, analogue or modification of an amino acid sequence in (a) to (f); and/or
(B) determining the decreased expression, modification, activity and/or concentration of at least one marker protein (a down-regulated marker protein) in a biological sample from the human, said marker protein selected from the group consisting of:
  (a) ATP synthase beta subunit or phosphorylated isoforms thereof;
  (b) creatine kinase B subunit;
  (c) myosin regulatory light chain 2 down-regulated isoform;

(d) a marker protein defined by the characteristics disclosed in table 3 (match nos: 199, or 391);

(e) an analogue having preferably at least 70% homology with any one of the polypeptides in (a), (b), (c) or (d) or a part thereof;

(f) a derivative, analogue or modification of an amino acid sequence in (a), (b), (c) or (d);

where the increased or decreased expression, modification, activity and/or concentration is relative to a value obtainable from a biological sample from a normal human. The biological sample can be selected from the group consisting of urine, blood, lymphatic fluids, saliva and tissue, preferably muscular tissue, e.g. from the vastus lateralis muscle. As the determination of whether a protein is up-regulated or down-regulated serves as useful indicators of susceptibility to a disease related to diabetes, the invention also relates to a method for diagnosing or determining the predisposition of at least one disease relating to diabetes, preferably type 2 diabetes, in a human, the method comprising determining the presence, activity, modification, concentration and/or level of expression of at least one marker protein (e.g. 1, 2, 3, 4, 5, 6, 7, 8, 9, 10 or more) which is present in a significantly lower or significantly higher amount in a sample from a person having a diabetes related disease than in a sample from a normal person. It should be understood that such marker proteins can be chosen from marker proteins identified by their peptide fragment and/or gel location (i.e. where no association to a particular gene has yet been made—possibly because the gene has not been identified). A person skilled in the art will be able to identify other marker proteins, using the methods disclosed in the examples.

In another embodiment, the invention relates to a method of determining the likelihood of an agent having a therapeutic effect in the treatment of a disease related to diabetes comprising determining the level of expression of one or more polypeptides according to the invention before and after exposing a test model to said agent and comparing said levels.

Further, the invention relates to a method of determining the effect of a compound in the treatment of a diabetes-related disease comprising determining the level of expression of one or more polypeptides (e.g. 1, 2, 3, 4, 5, 6, 7, 8, 9, 10 or more) according to the invention. Especially, such a method can be used to evaluate the effect of a compound used in the treatment of a diabetes-related disease comprising determining the level of expression of one or more marker proteins before and after exposing a test model to said agent.

A presently preferred method for determining the effect of a substance in treatment of a diabetes-related disease, is a method comprising using a mammal or part of this mammal, which has been established to be an individual having a high likelihood of having the disease or a predisposition (e.g. genetic) for having the disease, e.g. by use of a method according to the invention, the method comprising administering the substance to the mammal or part thereof and determining the effect of the substance, preferably by determining the level of one or more marker proteins according to the invention, before and after administering the substance to said mammal or part thereof.

The invention further relates to a method of determining the nature or cause of a diabetes-related disease in a human having or susceptible to said disease comprising establishing the level of expression of a marker protein according to the invention in relation to a model.

In another embodiment, the invention relates to a nucleic acid fragment which comprises:

(A) a nucleotide sequence which codes for a polypeptide or its regulatory elements, which polypeptide comprises at least one amino acid sequence selected from the group consisting of:

(a) ATP synthase beta subunit or phosphorylated ATP synthase beta subunit isoforms;

(b) phosphoglucomutase 1;

(c) heat shock protein 90 beta;

(d) creatine kinase B subunit;

(e) myosin regulatory light chain 2;

(f) collagen alpha1 (VI) chain;

(g) 78 kDa glucose-regulated protein;

(h) a marker protein defined by the characteristics disclosed in table 3 (match nos: 199, 303, 391, or 511);

(i) an analogue having preferably at least 70% homology with any one of the polypeptides in (a), (b), (c), (d), (e), (f), (g) or (h) or a part thereof; and (j) a derivative, precursor, analogue or modification of an amino acid sequence in (a) to (i); or (B) a nucleotide sequence which hybridizes with a nucleotide sequence according to (A), with a regulatory sequence to said nucleotide sequence or with the complementary strand to said sequence.

Such a nucleic acid fragment can be used for detecting the presence or level of a marker protein associated with a diabetes related disease; for detection of a nucleic acid sequence encoding said marker protein, e.g. as a probe or a primer for PCR, or as medication for regulation the expression or level of a marker protein, e.g. in antisense therapy or gene therapy. Also, such a sequence can be incorporated into a vector and used for producing the polypeptide by methods known to a person skilled in the art. Of course, the proteins can be produced by other methods, e.g. by solid state synthesis or by purification from natural sources, e.g. tissue.

In a still further embodiment, the invention relates to an antibody able to bind to a marker protein (or its modification product) according to the invention. The antibody can be polyclonal or monoclonal. Methods of obtaining such antibodies are known to a person skilled in the art. An antibody according to the invention can be used for detecting the presence or level of a marker protein associated with a diabetes-related disease, or it can be used as a therapeutic.

In a further embodiment, the invention relates to a test kit for diagnosing a diabetes-related disease or a predisposition, e.g. genetic, for said disease in a mammal, said test kit comprising:

(A) at least one binding means which specifically binds to at least one marker protein according to the invention, e.g. i) an antibody for said marker protein; ii) a nucleic acid fragment capable of binding to said marker protein; and/or iii) a compound (e.g. an antimimetic) capable of binding to said marker protein;

(B) at least one means for detecting binding, if any, or the level of binding, of a binding means to at least one of said marker proteins; and, if necessary, (C) at least one means for correlating whether binding, if any, or the level of binding, to said binding means is indicative of the individual mammal having a significantly higher likelihood of having the disease or a (genetic) predisposition for having the disease.

Also, the invention relates to a method for determining the effect of a substance in treatment of a diabetes-related disease, the method comprising using a mammal or part of this mammal, which has been established to be an individual having a high likelihood of having the disease or a predisposition (e.g. genetic) for having the disease (e.g. by use of the method of claim 1) the method comprising administering the substance to the mammal or part thereof and determining the effect of the substance, preferably by determining the level of one or more (e.g. 1, 2, 3, 4, 5, 6 or more) marker proteins according to the invention, before and after administering the substance to said mammal or part thereof.

It should be noted that the detection of any combination of more than one of the markers would be expected to make the analysis an even more reliable indicator for the disease related to diabetes. Thus, a method for diagnosing or determining the predisposition of at least one disease related to diabetes comprising determining the presence, activity, concentration and/or level of expression of a combination of two markers would be preferred and three or more markers (e.g. 4, 5, 6 or more markers) would be strongly preferred. It is analogously suggested that treatment with more than one compound (e.g. 2, 3, 4, 5, 6 or more compounds) according to the invention (e.g. more than one compound chosen from the group consisting of: a polypeptide, a nucleic acid fragment or an antibody according to the invention), said compounds combined being able to affect the level of more than one marker protein, would make the treatment of the disease even more efficient.

By the term "diabetes related disease" is understood any disease related to diabetes in its broadest sense, including complications to diabetes and components of the metabolic syndrome (prior to the onset of diabetes). Examples of complications related to type 2 diabetes mellitus are retinopathy, neuropathy, nephropathy, macroangiopathy, insulin resistance, hyperlipidemia, hypertension, and obesity. Examples of the metabolic syndrome are obesity, dyslipidemia, glucose intolerance hypertension and other cardiovascular diseases.

The term "polypeptide" in the present invention has its usual meaning. That is an amino acid chain of any length, including a full-length protein, oligopeptides, short peptides and fragments thereof, wherein the amino acid residues are linked by covalent peptide bonds. The terms "polypeptide", "peptide", "amino acid sequence" and "protein" are used interchangeably.

The polypeptide may be chemically or biochemically modified by being phosphorylated, methylated, sulphylated, glycosylated or by any other forms of modification, or by the addition of any form of lipid or fatty acid, ubiquitin or any other large side groups or by containing additional amino acids such as a signal peptide. Furthermore, the polypeptide may be cleaved e.g. by processing at its N- or C-termini or be spliced to remove an internal sequence.

Each polypeptide may thus be characterized by specific amino acids and be encoded by specific nucleic acid sequences. It will be understood that such sequences include analogues and variants produced by recombinant or synthetic methods wherein such polypeptide sequences have been modified by substitution, insertion, addition or deletion of one or more amino acid residues in the recombinant polypeptide and still being immunogenic in any of the biological assays described herein. Substitutions are preferably "conservative". Conservative substitutions are known to a person skilled in the art. Preferably, amino acids belonging to the same grouping (non-polar (G, A, P, I, L and V), polar-uncharged (C, S, T, M, N and Q), polar-charged (D, E, K and R) and aromatic (H, F, W and Y)). Within these groups, amino acids may be substituted for each other, but other substitutions are of course possible.

Each polypeptide is encoded by a specific nucleic acid sequence. It will be understood that such sequences include analogues and variants hereof wherein such nucleic acid sequences have been modified by substitution, insertion, addition or deletion of one or more nucleic acid residues (including the insertion of one or more introns (small or large)). Substitutions are preferably silent substitutions in the codon usage, which will not lead to any change in the amino acid sequence, but may be introduced to enhance the expression of the protein.

In the present context the term "substantially pure polypeptide fragment" means a polypeptide preparation which contains at most 5% by weight of other polypeptide material with which it is natively associated (lower percentages of other polypeptide material are preferred, e.g. at most 4%, at most 3%, at most 2%, at most 1%, and at most ½%). It is preferred that the substantially pure polypeptide is at least 96% pure, i.e. that the polypeptide constitutes at least 96% by weight of total polypeptide material present in the preparation, and higher percentages are preferred, such as at least 97%, at least 98%, at least 99%, at least 99.25%, at least 99.5%, and at least 99.75%. It is especially preferred that the polypeptide fragment is in "essentially pure form", i.e. that the polypeptide fragment is essentially free of any other protein with which it is natively associated, i.e. free of any other protein from a mammal. This can be accomplished by preparing the polypeptide of the invention by means of recombinant methods in a host cell as known to a person skilled in the art, or by synthesizing the polypeptide fragment by the well-known methods of solid or liquid phase peptide synthesis, e.g. by the method described by Merrifield (Merrifield, R. B. Fed. Proc. Am. Soc. Ex. Biol. 21: 412, 1962 and J. Am. Chem. Soc. 85: 2149, 1963) or variations thereof, or by means of recovery from electrophoretic gels.

The invention also encompasses isoforms, derivatives, precursors, truncates (such as mature forms), analogues and mimetics of the above mentioned polypeptides. Such an isoform, derivative, analogue and mimetic preferably have the same activity, e.g. the same kind of enzymatic activity, as the polypeptide from which it is derived. The isoform, derivative, analogue or mimetic can have a lower level of activity, the same level or preferably, a higher level of activity than the parent polypeptide.

The term "isoform" refers to a family of related proteins (i.e. multiple forms of the same protein) that differ somewhat in their amino acid sequence. They can be produced by different genes or by alternative splicing of RNA transcripts from the same gene. Thus, the term "isoform" comprises homologous sequences of amino acid residues interspersed with variable sequences. Also, the term "isoform" comprises a form of the protein which has been post translationally processed, e.g. phosphorylated (phospho-isoform).

A "peptide mimetic" is a molecule that mimics the biological activity of a peptide but is no longer peptidic in chemical nature. By strict definition, a peptidomimetic is a molecule that no longer contains any peptide bonds (that is, amide bonds between amino acids). However, the term peptide mimetic is sometimes used to describe molecules that are no longer completely peptidic in nature, such as pseudo-peptides, semi-peptides and peptoids. Whether completely or partially non-peptide, peptidomimetics according to this invention provide a spatial arrangement of reactive chemical moieties that closely resembles the three-dimensional arrangement of active groups in the peptide on which the peptidomimetic is based. As a result of this similar active-site geometry, the peptidomimetic has effects on biological systems, which are similar to the biological activity of the peptide. The present invention encompasses peptidomimetic compositions which are analogs that mimic the activity of biologically active peptides according to the invention, i.e. the peptidomimetics can be used for treatment of diabetes related diseases. The peptidomimetic of this invention are preferably substantially similar in both three-dimensional shape and biological activity to the peptides or active sites of such as set forth above.

Alternatively, the mimetic can be an 'antimimetic'. In other words, a molecule that can fit into and block the active site of the protein, or bind to binding sites or sites of interaction with other biological molecules and so interfere with the function of the protein. Most current drugs are of this type. Such antimimetics that are capable of interacting with the polypeptides of the invention are encompassed by the present invention.

An aptamer is a compound that is selected in vitro to bind preferentially to another compound (in this case the identified proteins). Often, aptamers are nucleic acids or peptides because random sequences can be readily generated from nucleotides or amino acids (both naturally occurring or synthetically made) in large numbers but of course they need not be limited to these.

There are clear advantages for using a mimetic of a given peptide rather than the peptide itself, because peptides commonly exhibit two undesirable properties: (1) poor bioavailability; and (2) short duration of action. Peptide mimetics offer an obvious route around these two major obstacles, since the molecules concerned are small enough to be both orally active and have a long duration of action. There are also considerable cost savings and improved patient compliance associated with peptide mimetics, since they can be administered orally compared with parenteral or transmucosal administration for peptides. Furthermore, peptide mimetics are much cheaper to produce than peptides. Finally, there are problems associated with stability, storage and immunoreactivity for peptides that are not experienced with peptide mimetics.

Thus, the peptides described above have utility in the development of such small chemical compounds with similar biological activities and therefore with similar therapeutic utilities. The techniques of developing peptidomimetics are conventional. Thus, peptide bonds can be replaced by non-peptide bonds that allow the peptidomimetic to adopt a similar structure, and therefore biological activity, to the original peptide. Further modifications can also be made by replacing chemical groups of the amino acids with other chemical groups of similar structure. The development of peptidomimetics can be aided by determining the tertiary structure of the original peptide by NMR spectroscopy, crystallography and/or computer-aided molecular modelling. These techniques aid in the development of novel compositions of higher potency and/or greater bioavailability and/or greater stability than the original peptide [Dean (1994), BioEssays, 16: 683-687; Cohen and Shatzmiller (1993), J. Mol. Graph. 11: 166-173; Wiley and Rich (1993), Med. Res. Rev., 13: 327-384; Moore (1994), Trends Pharmacol. Sci., 15: 124-129; Hruby (1993), Biopolymers, 33: 1073-1082; Bugg et al. (1993), Sci. Am., 269: 92-98, all incorporated herein by reference]. Once a potential peptidomimetic compound is identified, it may be synthesized and assayed using the diagnostic assay described herein or an appropriate disease suppressor assay [see, Finlay et al. (1983), Cell, 57: 1083-1093 and Fujiwara et al. (1993), Cancer Res., 53: 4129-4133, both incorporated herein by reference], to assess its activity.

Thus, through use of the methods described above, the present invention provides compounds exhibiting enhanced therapeutic activity in comparison to the polypeptides described above. The peptidomimetic compounds obtainable by the above methods, having the biological activity of the above named peptides and similar three dimensional structure, are encompassed by this invention. It will be readily apparent to one skilled in the art that a peptidomimetic can be generated from any of the modified peptides previously described or from a peptide bearing more than one of the modifications previously described. It will furthermore be apparent that the peptidomimetics of this invention can be further used for the development of even more potent non-peptidic compounds, in addition to their utility as therapeutic compounds.

By the terms "nucleic acid fragment" and "nucleic acid sequence" are understood any nucleic acid molecule including DNA, RNA, LNA (locked nucleic acids), PNA, RNA, dsRNA and RNA-DNA-hybrids. Also included are nucleic acid molecules comprising non-naturally occurring nucleosides. The term includes nucleic acid molecules of any length, e.g. from 10 to 10000 nucleotides, depending on the use. When the nucleic acid molecule is for use as a pharmaceutical, e.g. in DNA therapy, or for use in a method for producing a polypeptide according to the invention, a molecule encoding at least a part of the polypeptide is preferably used, having a length from about 18 to about 1000 nucleotides, the molecule being optionally inserted into a vector. When the nucleic acid molecule is used as a probe, as a primer or in antisense therapy, a molecule having a length of 10-100 is preferably used. According to this invention, other molecule lengths can be used, for instance a molecule having at least 12, 15, 21, 24, 27, 30, 33, 36, 39, 42, 50, 60, 70, 80, 90, 100, 200, 300, 400, 500 or 1000 nucleotides (or nucleotide derivatives), or a molecule having at most 10000, 5000, 4000, 3000, 2000, 1000, 700, 500, 400, 300, 200, 100, 50, 40, 30 or 20 nucleotides (or nucleotide derivatives). It should be understood that these numbers can be freely combined to produce ranges.

The term "stringent" when used in conjunction with hybridization conditions is as defined in the art, i.e. the hybridization is performed at a temperature not more than 15-20° C. under the melting point (Tm) of the nucleic acid fragment, cf. Sambrook et al Molecular Cloning; A laboratory manual, Cold Spring Harbor Laboratories, NY, 1989, pages 11.45-11.49. Preferably, the conditions are "highly stringent", i.e. 5-10° C. under the melting point (Tm).

Throughout this specification, unless the context requires otherwise, the word "comprise", or variations thereof such as "comprises" or "comprising", will be understood to imply the inclusion of a stated element or integer or group of elements or integers but not the exclusion of any other element or integer or group of elements or integers.

The term "sequence identity" indicates a quantitative measure of the degree of homology between two amino acid sequences of equal length or between two nucleotide sequences of equal length. If the two sequences to be compared are not equal length, they must be aligned to best possible fit with the insertion of gaps or alternatively truncation at the end of the protein sequences. The sequence identity can be calculated as $$\frac{(N_{ref} - N_{dif})100}{N_{ref}},$$

wherein $N_{dif}$ is the total number of non-identical residues in the two sequences when aligned and wherein $N_{ref}$ is the number of residues in one of the sequences. Hence, the DNA sequence AGTCAGTC will have a sequence identity of 75% of the sequence AATCAATC ($N_{dif}$=2 and $N_{ref}$=8). Sequence identity can alternatively be calculate by the blast program e.g. the BLASTP program (Pearson W. R and D. J. Lipman (1988) PNAS USA 85:2444-2448. In one aspect of the invention, alignment is performed with the sequence alignment method Clustalw with default parameters as described by Thompson J., et al Nucleic Acids Res 1994 22: 4673-4680.

A preferred minimum percentage of sequence identity is at least 70%, such as at least 80%, at least 85%, at least 90%, at least 91%, at least 92%, at least 93%, at least 94%, at least 95%, at least 96%, at least 97%, at least 98%, at least 99%, and at least 99.5%.

The invention also relates to the use of a polypeptide or nucleic acid of the invention for use as therapeutic vaccines as have been described in the literature exemplified by Lowry, D. B. et al 1999, Nature 400: 269-71.

A monoclonal or polyclonal antibody, which is specifically reacting with a polypeptide of the invention in an immuno assay, or a specific binding fragment of said antibody, is also part of the invention. The antibodies can be produced by methods known to a person skilled in the art. The polyclonal antibodies can be raised in a mammal, for example, by one or more injections of a polypeptide according to the present invention and, if desired, an adjuvant. The monoclonal antibodies according to the present invention may, for example, be produced by the hybridoma method first described by Kohler and Milstein, Nature, 256:495 (1975), or may be produced by recombinant DNA methods such as described in U.S. Pat. No. 4,816,567. The monoclonal antibodies may also be isolated from phage libraries generated using the techniques described by McCafferty et al, Nature, 348:552-554 (1990), for example. Methods for producing antibodies are described in the literature, e.g. in U.S. Pat. No. 6,136,958.

In diagnostics, an antibody, a nucleic acid fragment and/or a polypeptide of the invention can be used either alone, or as a constituent in a composition. Such compositions are known in the art, and comprise compositions in which the antibody, the nucleic acid fragment or the polypeptide of the invention is coupled, preferably covalently, to at least one other molecule, e.g. a label (e.g. radioactive or fluorescent) or a carrier molecule.

The present invention is further directed to methods for using the compounds described above to therapeutically and/or prophylactically treat a patient for a diabetes related disease.

The methods of the present invention include the steps of: a) incorporating one or more of the compounds of the present invention in a suitable pharmaceutical carrier; and b) administering either a therapeutically effective dosage or a prophylactically effective dosage of the compound or compounds incorporated in the carrier to a patient.

The term "suitable pharmaceutical carrier" refers to any carrier known in the pharmaceutical arts for administration of compounds to a patient. Any suitable pharmaceutical carrier can be used according to the present invention, so long as compatibility problems do not arise.

Administration of an effective dosage to a patient can be accomplished by parenteral injection, such as intravenously, intrathecally, intramuscularly or intra-arterially. The compounds can also be administered orally or transdermally, or by any other means known to those skilled in the art, e.g. by means of an inhalator or a nasal spray. Oral administration is presently preferred.

As used herein, the term "therapeutically effective amount" refers to that amount of one or more of the compounds of the present invention required to therapeutically treating a patient. Such treatment is appropriate for subjects having a diagnosed diabetes related disease. Similarly, the term "prophylactically effective amount" refers to that amount of one or more of the compounds of the present invention needed to prophylactically treat a patient. Such treatment is appropriate for subjects who, for example, have not yet established any clinical symptoms of a diabetes related disease. It could be advantageous to start a prophylactic treatment as soon it is determined that the subject is in risk for developing a diabetes related disease, e.g. by means of determination of a predisposition for diabetes by having an altered level of markers.

As will be appreciated by a person skilled in the art, the dosage of a compound given, the route of administration and the duration of therapy will be dependent on not only the type of compound and its effectiveness in treating the disease but also upon the individual being treated, taking into consideration such factors as the body weight of the patient, other therapies being employed to treat the patient, and the condition, clinical response and tolerance of the patient. Dosage, administration, and duration of therapy can be determined by one skilled in the art upon evaluation of these and other relevant factors.

Determination of the levels of the found markers of type 2 diabetes on a muscle biopsy specimen from a subject genetically prone to develop type 2 diabetes can be used to determine the need for intervention in order to prevent type 2 diabetes or to treat the prediabetic state in the form of medical treatment, guidelines for diet, physical activity etc. If for example the levels of the down-regulated phospho-isoform of ATP synthase beta subunit described above is less than 0.5 % of the total protein-related IOD on a 2D-gel image (from an IPG gel covering the pH range from 4 to 7 prepared as described herein), the probability of having type 2 diabetes or a prediabetic state is greater than 85%. In the same way, if the levels of creatine kinase B is less than 0.25 %IOD on a 2D-gel image, the probability of having type 2 diabetes or a prediabetic state is greater than 80%. And if the levels of both markers of type 2 diabetes are lower than these levels the probability of having type 2 diabetes or a prediabetic state is even greater.

Substances (hormones, kinases, phosphatases, small molecules etc.) that can modulate the phosphorylation and/or expression of ATP synthase beta-subunit are under investigation. Substances that modulate the phosphorylation and/or expression of ATP synthase beta-subunit in a manner that results in improvements of the physiological parameters related to type 2 diabetes such as insulin sensitivity, glucose uptake and blood glucose can be used directly, whereas substances with the opposite effect can be used for the development of inhibitors. Our studies suggest that therapeutic activation of the kinase, which phosphorylates ATP synthase beta-subunit, will result in improved ATP synthesis, with subsequent improvements in insulin sensitivity, glucose uptake and blood glucose.

BRIEF DESCRIPTION OF THE SEVERAL VIEWS OF THE DRAWINGS

FIG. 2: Phosphorylation of ATP synthase β-subunit (ATPsyn-β) in human skeletal muscle

FIG. 2C: The sequence coverage of this more abundant ATPsyn-β isoform was 59% and 29 out of 45 measured peptides were matched to this protein as indicated (bold). The potential phosphorylation site of the phosphorylated peptide (marked by a box) was Thr213 within the nucleotide-binding region (underlined).

FIG. 3: Potential roles for the observed protein markers of type 2-diabetes in skeletal muscle metabolism

EXPERIMENTIAL

Figure 1:
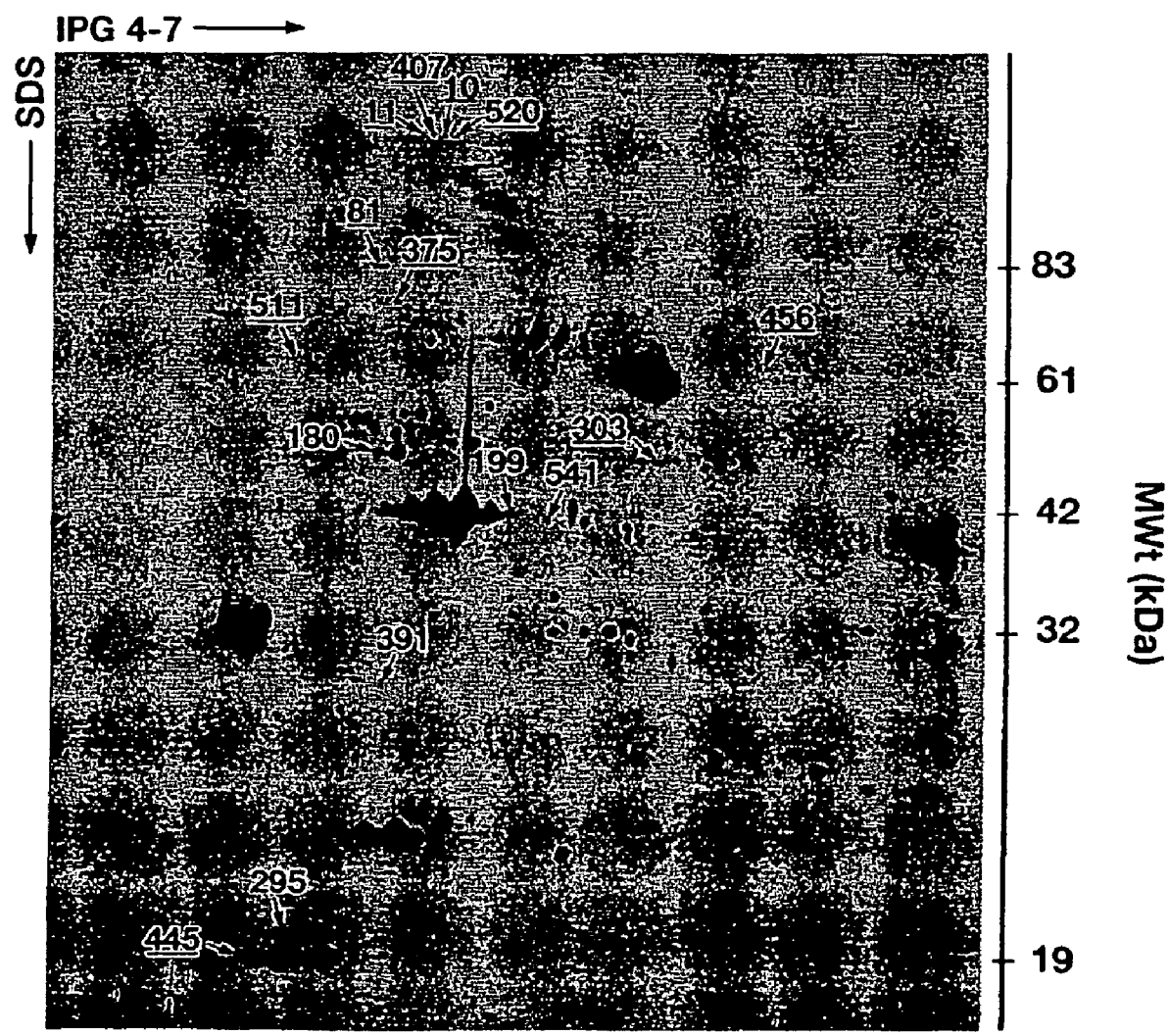
FIG. 1: Protein markers of type 2-diabetes in skeletal muscle Representative 2D gel image of human skeletal muscle from a diabetic subject. Protein spots were separated in the first dimension by IPG gels (pI 4-7) and visualised by silver staining. The numbers correspond to the protein spots that were significantly up-regulated (underlined) or down-regulated in muscle of type 2-diabetic subjects. Of these fifteen proteins, eleven were identified by MALDI-MS (Table 2).

Proteome analysis offers the possibility to study thousands of proteins as well as their post-translational modifications simultaneously, and is a promising technique in the study of complex diseases such as type 2 diabetes (5). The high-resolution proteome technology effectively separates and identifies proteins with high success rate. Compared to analyses of mRNA expression, proteome analysis offer the possibility of relative quantification of changes in protein expression as well as identification and quantitation of post-translatory protein modification such as phosphorylation, methylation and cleavage. Post-translational modifications are often required for the functional activation of a protein and hence, may be of pathogenetic importance.

The present inventors have used proteome analysis to select and identify proteins associated to diabetes. These proteins, in themselves, either up-regulated or down-regulated, are indicators of diabetes in a patient. The pattern of regulation of a grouping of these proteins also serves as an indicator of diabetes. These proteins can be used as targets for the treatment of diabetes or they can be used as therapeuticals for treatment of the disease.

Thus, the determination of whether a protein is up-regulated or down-regulated serves as useful indicators of diabetes susceptibility. The pattern of up and down regulation may also serve as an indicator. That is to say that the level of expression of more than one protein is established and the pattern of expression of a grouping of proteins is used as an indicator. Obviously, the reliability of identification increases as the number in the group increases.

Muscle Samples

Muscle samples were collected from 10 type 2 diabetic (diabetes group) and 10 healthy subjects (control group). Subjects with type 2 diabetes (fasting C-peptide>600 pmol/l and GAD65 antibody negative) were treated by diet only or in combination with oral antidiabetics, which were withdrawn 2 weeks before the study. Subjects were instructed to refrain from excessive physical exercise for 48 h and to fast for 10 h (overnight) before the study. Normal glucose tolerance was confirmed in non-diabetic subjects and fasting concentrations of plasma glucose and FFA and serum insulin and C-peptide were assayed as described previously (26). Percutaneous needle biopsy of the vastus lateralis muscle was performed with a biopsy pistol, and the muscle specimens (~25 mg) were immediately blotted free of blood, fat and connective tissue and frozen in liquid nitrogen. The study protocol was performed in accordance with the Helsinki Declaration.

Sample Preparation

The frozen muscle samples were homogenized for 25 min in 100 μl of icecold DNase/RNase buffer (20mmol/l Tris-HCl buffer pH 7.5 containing 30 mmol/l NaCl, 5 mmol/l $CaCl_2$, 5 mmol/l $MgCl_2$ and 25 μg/ml RNase A/DNase I (Worthington, Freehold, N.J.)). After homogenization, the samples were lyophilized overnight and then dissolved in 120 μl of lysis buffer (7 M urea (ICN Biomedicals), 2 M thiourea (Fluka), 2% CHAPS, 0.4% DTT (Sigma), 0.5% Pharmalyte 3-10 and 0.5% Pharmalyte 6-11 (Amersham Pharmacia Biotech, Sweden)) under continuous shaking.

Protein and CPM Determination

The protein concentration in the samples was determined using the Bradford method, which was adopted for use with lysis buffer as described before (29).

Two Dimensional Electrophoresis

First dimension gel electrophoresis was performed on IPG 4-7 gradient gels (Amersham Pharmacia Biotech). Rehydration buffer for IPG4-7 strips was identical with lysis buffer used for sample preparation and the sample was applied by in-gel rehydration. 400 μg of protein was loaded on each gel. Focusing was performed on Multiphor II at 20° C. using voltage/time profile linearly increasing from 0 V to 600 V for 2:15 h, from 600 V to 3500 V for 1 h and 3500 V for 13:30 h. After focusing, strips were equilibrated two times 15 min in equilibration buffer (6M urea, 2% SDS, 30% Glycerol, 50 mM Tris-HCL pH 8.8, 1% DTT). The gels were kept frozen in −80° C. between the equilibration steps. SDS PAGE second dimension was performed using Protean II Multi Cell 2-D Electrophoresis System (Bio-Rad) and laboratory-made single percentage gels (12.5% acrylamide; acrylamide: N,N'-ethylene-bis-acrylamide ratio 200:1). The gels were run overnight at 20° C. at constant current. Running buffer was recirculated to maintain pH, temperature and salt concentrations.

Protein Visualization and Computer Analysis

After the second dimension, proteins were visualized using silver-staining method as described (29). All gel images were analyzed by the same person using Bio Image computer program (version 6.1, B. I. System Corporation). The expression of each protein was measured and expressed as its percentage integrated optical density (%IOD) (a percentage of the sum of all the pixel grey level values within boundary of the spot in question compared to that of all detected spots). For comparison, the present inventors have used 6 gels from the control group and 9 from the diabetes group (the remaining gels revealed protein degradation that occurred during the sample preparation procedure and thus could not be used). Images from each group were matched and compared. The average value of spot %IOD and standard deviation for each protein in each group were calculated and then compared using Student's t-test. Protein spots whose expression was found different at the significance level of 95% were selected for further analysis.

Mass Spectrometric Protein Identification

Proteins of interest were cut out from gels and after in-gel digestion analysed by MALDI mass spectrometry (27, 28, 29). The obtained mass spectra were internally calibrated using trypsin autodigestion peptides and the masses were used to search NOBI database using the ProFound and further analysed with FindPept and FindMod programs (www.proteometrics.com). Database searches were performed using the following attributes with minor modification needed for each program: all species, no restrictions for molecular weight and protein pI, trypsin digest, one missed cleavage allowed, cysteines modified by acrylamide, and oxidation of methionines possible, mass tolerance between 0.1-0.5 Da. Identification was considered positive, when at least 5 peptides matched the protein with no sequence overlap.

[$^{32}$P]-Labelling of Human Myoblasts

Human skeletal muscle cell cultures were established as previously described (Hemmer et al, 30). Myoblasts were grown in 12-wells plates, and growing cell medium was changed to DMEM containing 5 mM glucose and supplemented with 10% foetal calf serum 1 day before the labelling experiment. Prior to labelling, cells were incubated in serum-free DMEM medium containing 0.2 % bovine serum albumin (BSA) for 2.5 hours. Phosphate groups in proteins of human myoblasts were biosynthetically labelled by incubating the myoblasts in 300 µl serum-free phosphate-free DMEM medium (ICN, Ohio) supplemented with 2 mM L-glutamine (Life Technologies, Paisley, Scotland), 0.2% BSA and 300 µCi [$^{32}$P]-orthophosphate (Amersham Biosciences) for 2.5 h. Immediately after, labelling medium was removed and cells were lysed in 400 µl lysis buffer as described above. Determination of [$^{32}$P]-orthophosphate incorporation into myoblast proteins was performed using TCA (trichloroacetic acid) precipitation as described (29). Two-dimensional electrophoresis was run as described above loading a cell lysate volume corresponding to 4×10$^5$ cpm on the gel. [$^{32}$P]-labelled proteins of myoblasts were visualised by exposing dried gels to phosphoimager plates (AGFA).

Results

The present inventors collected biopsies of the vastus lateralis muscle from age and gender matched control and type 2 diabetic (DM2) subjects to compare the in vivo protein expression profile of resting skeletal muscle in the postabsorptive state by proteome analysis (Table 1). The present inventors separated muscle proteins by two-dimensional (2D) gel electrophoresis and proteins were visualized by silver-staining method. The present inventors were able to match and quantitate 489 spots in each gel image using computerized image analysis. Fifteen protein spots were expressed at statistically different levels in the two groups (FIG. 1). These protein markers for DM2 were excised from the 2D gels, and following in gel tryptic digestion, submitted to matrix assisted laser desorption/ionization-time of flight mass spectrometry (MALDI-TOF-MS) and database searching for identification. Eleven of them have been identified; three metabolic enzymes, two chaperone proteins, and isoforms of two structural proteins (Table 2).

Phoshoglucomutase 1 (PGM-1) was significantly up-regulated in DM2 subjects (table 2). PGM1 is a glycolytic enzyme, that plays a pivotal role in glycogen metabolism.

The present inventors found that expression of heat-shock protein 90 beta (HSP90β) was significantly up-regulated in muscle from DM2 subjects (Table 2). The type of stress that increases expression of HSP90β in diabetic muscle is currently unknown.

One isoform of myosin regulatory light chain 2 (MRLC2) was significantly down-regulated while another isoform of MRLC2 was significantly up-regulated in DM2 subjects (Table 2). The function of MRLC2 in skeletal muscle is only partially understood. The potential implications of these changes in expression of MRLC2 isoforms are therefore unclear.

The down-regulated isoform of MRLC2 is identified as the ventricular/cardiac muscle isoform of MRLC2 (database accession number P10916), and the up-regulated isoform is identified as another isoform having the database accession number AAK52797. There is only 72% homology between the two isoforms.

Creatine kinase B (CK-B) was significantly down-regulated in DM2 subjects (Table 2). The present inventors found a negative correlation between plasma glucose and CK-B levels (FIG. 3C) in diabetic muscle suggesting a role for CK-B in glycolysis during hyperglycemia. In addition, the present inventors found a positive correlation of CK-B with the down-regulated ATPsyn-β phosphoisoform (FIG. 3D) in DM2 subjects.

Figure 2A:
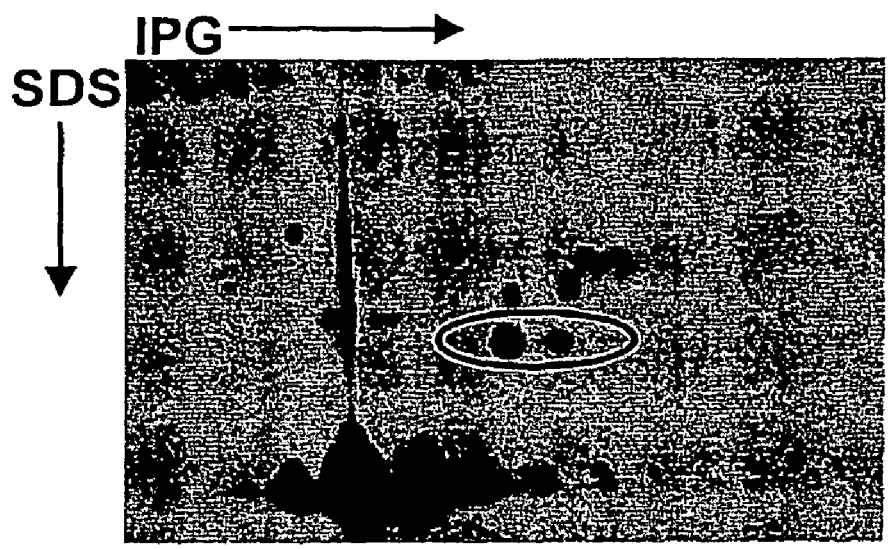
FIG. 2A: Comparison of enlarged regions of a silver-stained 2D gel of skeletal muscle and a [$^{32}$P]-labelled 2D gel of cultured human skeletal muscle cells (myoblasts) showing that all four isoforms are phosphorylated isoforms of ATPsyn-β.
Figure 2A:
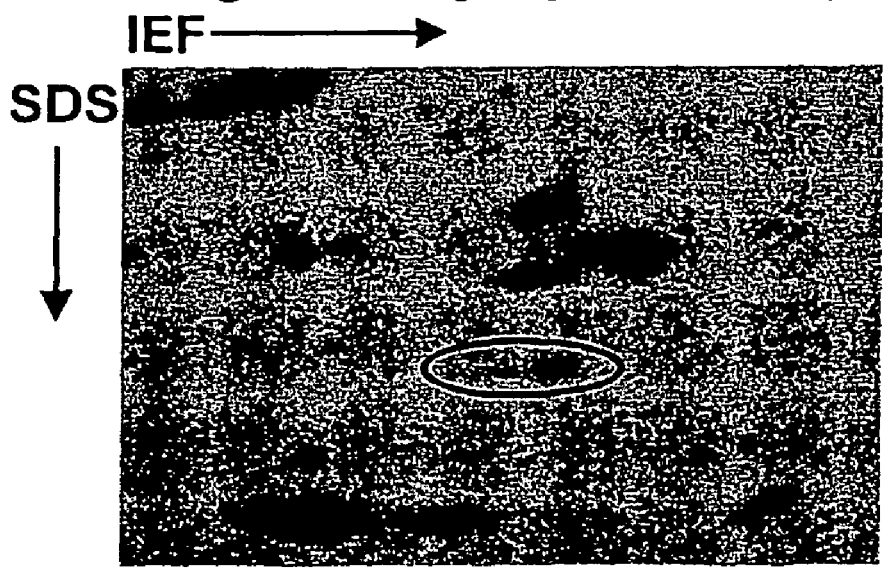
Figure 2B:
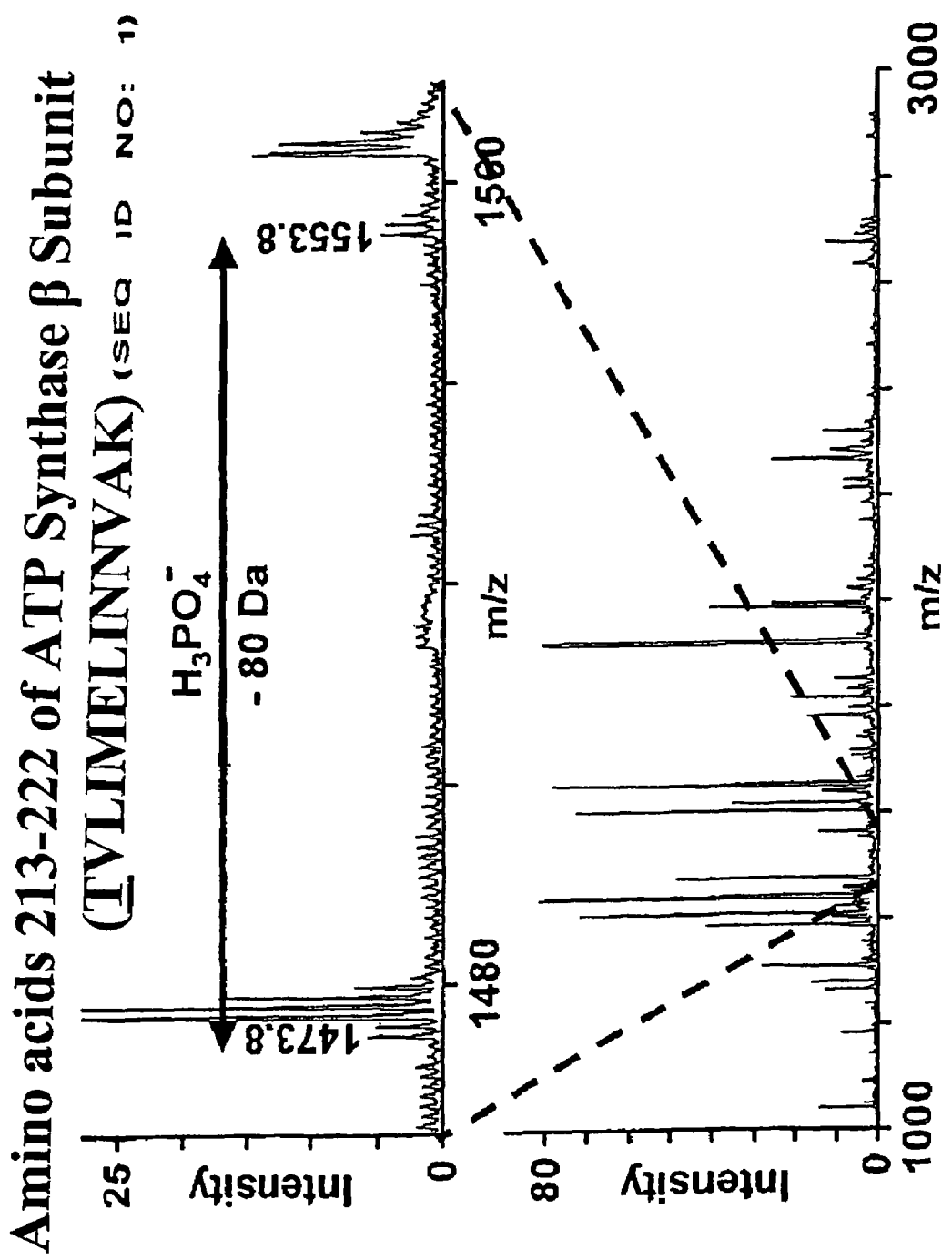
FIG. 2B: The large spot located to the right of ATPsyn-β (spot 180) on the silver-stained gel was also identified as an ATPsyn-β isoform by MALDI-TOF MS analysis. The MALDI peptide mass map of this ATPsyn-β isoform showed the presence of a phosphorylated peptide (two peaks with a mass difference of 80 Da) with the most probable phosphorylation site being threonine at the N-terminal end of the peptide.

The spot identified as ATP synthase beta subunit (ATPsyn-β) was significantly down-regulated in DM2 subjects (Table 2), and appeared within a series of four spots with identical molecular weights but different pI values, indicating heterogenous charge variants of the same protein (FIG. 2A). To further characterize the modification of ATP synthase β-subunit, we carried out 2-D gel electrophoresis of [$^{32}$P]-labelled human skeletal muscle cells (myoblasts). These 2-D gels revealed that all of the four identified ATPsynβ isoforms are in fact phosphorylated isoforms (FIG. 2A), and that a putative non-modified variant was below the level of detection by silver staining. MALDI-MS analysis and database searching for phosphopeptides from the tryptic digest of the three most basic phospho-isoforms of ATPsynβ, including the down-regulated ATPsynβ spot (no. 180), clearly demonstrated the presence of a phosphorylated residue most likely at position Thr213 in the nucleotide-binding domain of ATPsynβ (FIG. 2B-C). Tyrosine sulphation may give rise to the same pattern on 2-D gels and the same increase in peptide mass (80 Da) as phosphorylation. However, using the consensus features of a tyrosine sulphation site (31, 32), such sites were excluded in the sequence of ATPsynβ.

The [$^{32}$P]-labelling of all 4 ATPsynβ isoforms and the mass spectrometry data therefore indicate that ATPsynβ is regulated by multisite phosphorylation, and the present data demonstrate that the catalytic β-subunit of human F1-ATP synthase is regulated by phosphorylation in skeletal muscle, and that this regulation might be altered in DM2.

Also, 78-kDA glucose-regulated protein (GRP78) was significantly up-regulated in muscle tissue of patients with type 2 diabetes. We observed increased levels of GRP78 in type 2 diabetic subjects, and of the three isoforms identified only the most basic (non-phosphorylated) and most active isoform was significantly up-regulated.

Four spots, each presumably representing an isoform of alpha-1 chain of type VI collagen (α1(VI) collagen), demonstrated that this protein and isoforms thereof were significantly up-regulated in patients with type 2 diabetes.

Figure 3A:
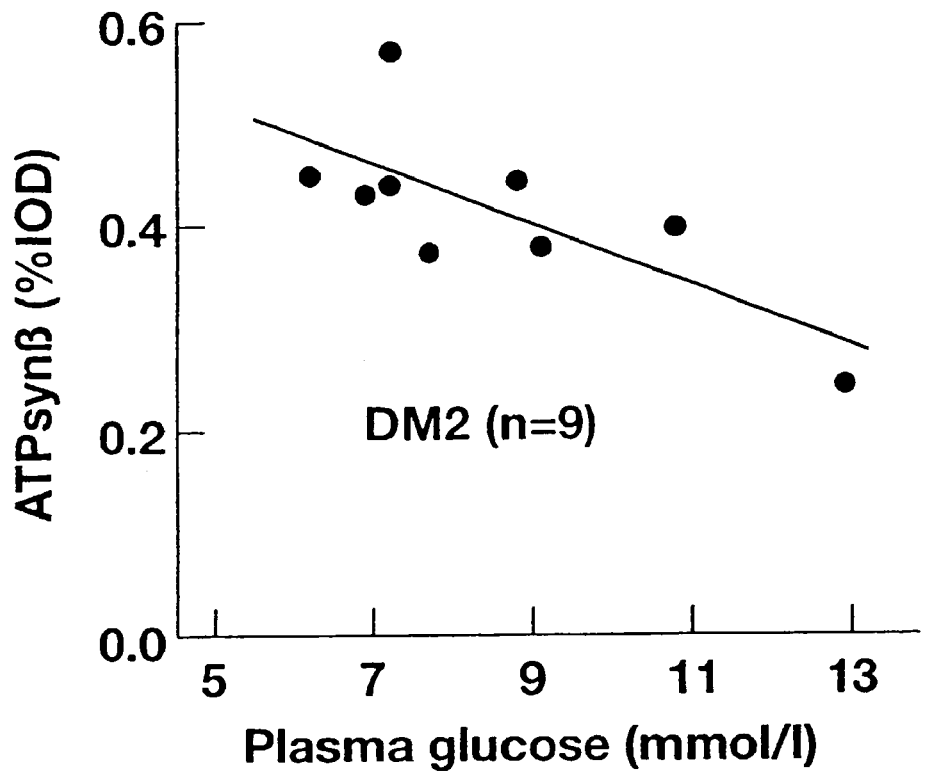
FIG. 3A-3B: Correlation between expression of the down-regulated ATP synthase β-subunit (ATPsyn-β) isoform and fasting plasma glucose levels in DM2 subjects (r=−0.75; P=0.020), and fasting plasma FFA levels in control subjects (r=−0.81; P=0.049).
Figure 3B:
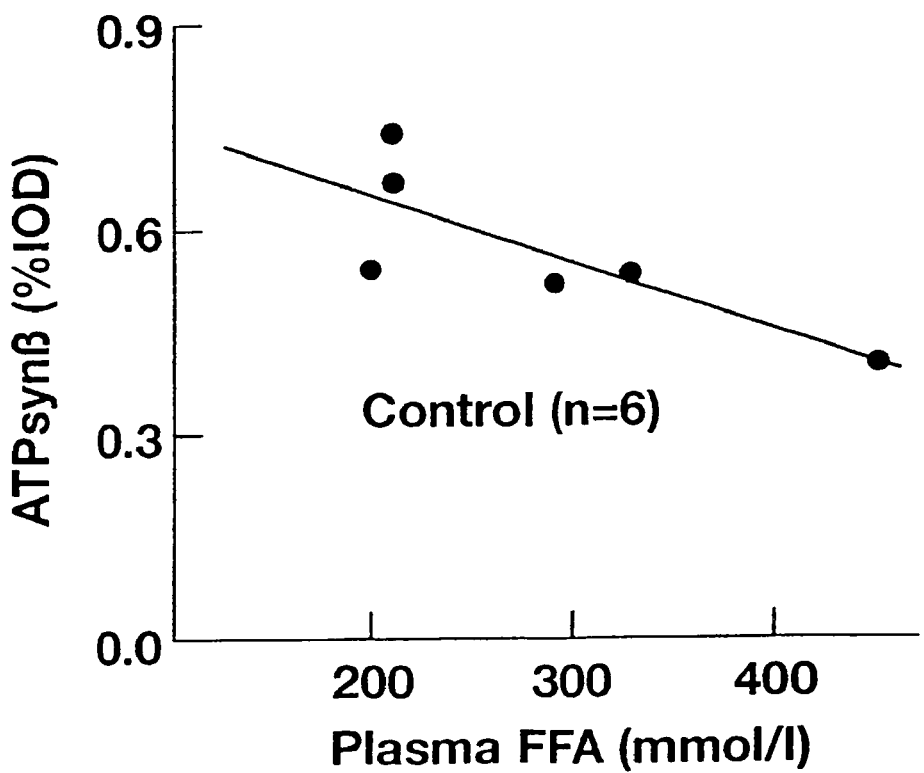
Figure 3C:
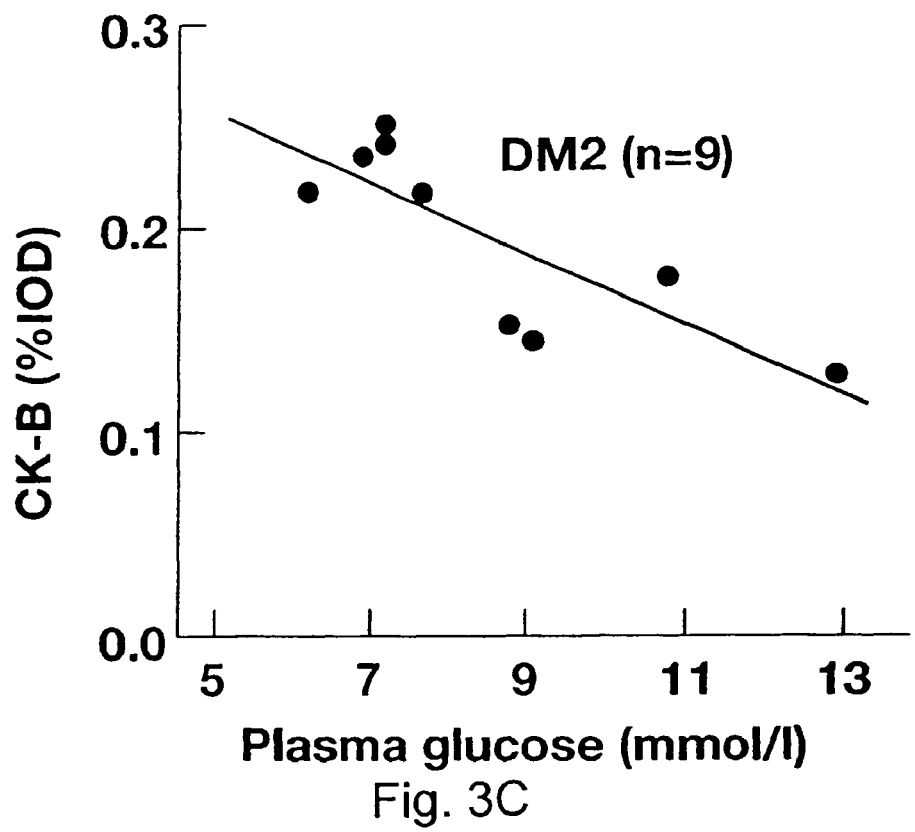
FIG. 3C-3D: Correlation between expression of creatine kinase B and fasting plasma glucose levels (r=−0.82; P=0.007) and expression of the down-regulated ATPsyn-β isoform (r=0.71; P=0.033) in DM2 subjects.
Figure 3D:
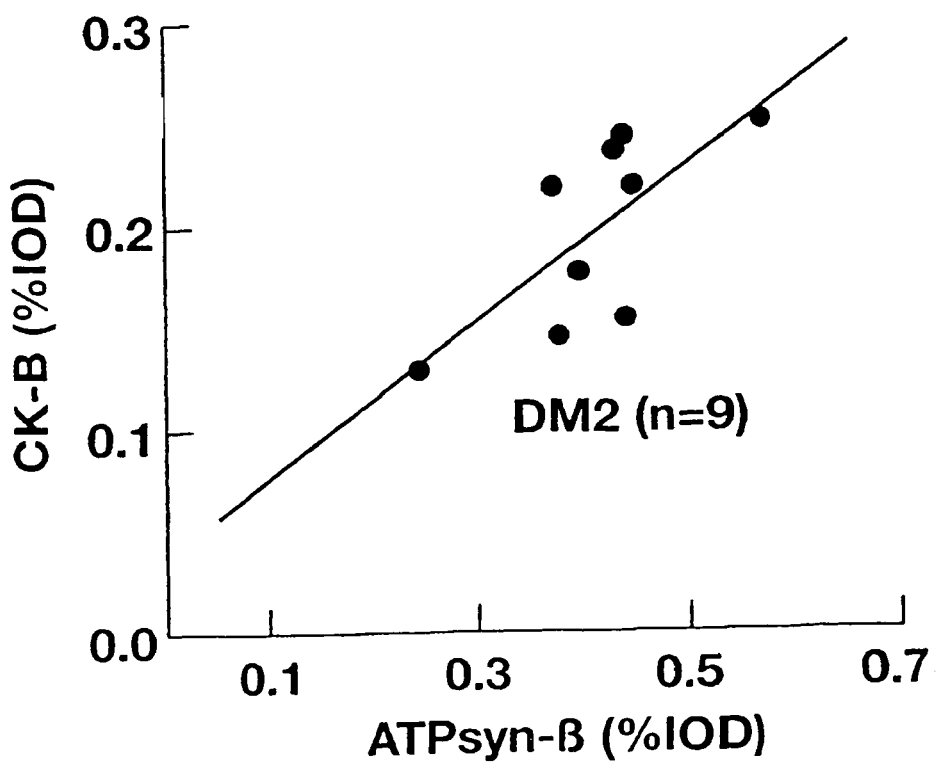
Figure 3E:
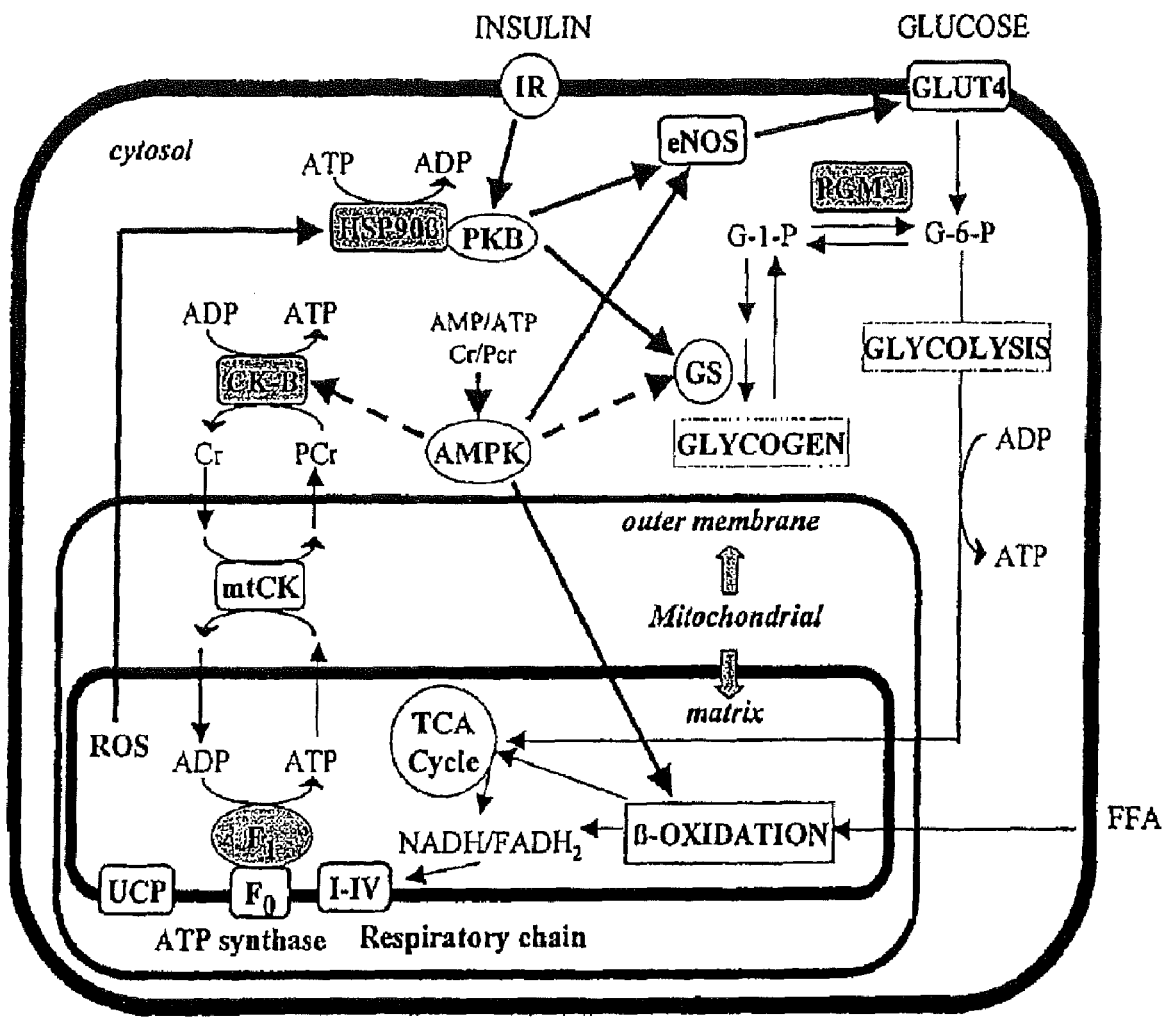
FIG. 3E: Proposed scheme for the putative roles of the protein markers of type 2 diabetes (marked with grey) in skeletal muscle metabolism. The $F_1$ portion of ATP synthase contains the three catalytic β-subunits, and complex IV of the respiratory chain is identical to cytochrome C oxidase. ROS, reactive oxygen species; PKB, protein kinase B; eNOS, endothelial nitric oxide synthase; AMPK, AMP-activated protein kinase; TCA cycle, tricarboxylic acid cycle; mtCK, mitochondrial creatine kinase; GLUT4, glucose transporter 4; GS, glycogen synthase; IR, insulin receptor; G-6-P, glucose-6-phosphate and G-1-P, glucose-1-phosphate. Remaining abbreviations are explained in the text section.
Figure 4:
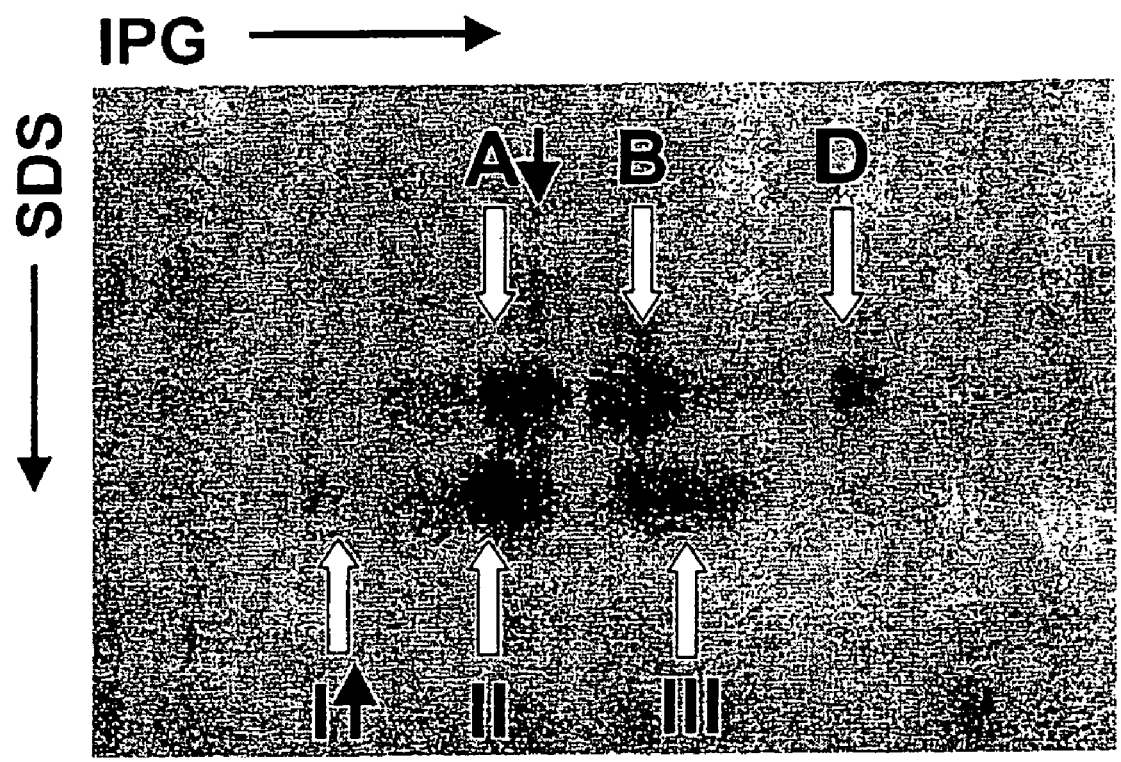
FIG. 4: Two different MRLC2 isoforms differently expressed in diabetic muscle Spot A was down-regulated, whereas spot I was up-regulated in DM2 subjects. Spots A, B and C were all identified by MALDI-MS as the MRLC2 ventricular/cardiac muscle isoform (database acc. no: P10916) and probably represent different phospho-isoforms. Spots I, II and III were all identified as another MRLC2 isoform (database acc. no: AAK52797), and they probably also represent different phospho-isoforms. There is only 72% homology between the two different isoforms of MRLC2.

In control subjects the present inventors observed a negative correlation between the down-regulated expression levels of the ATPsyn-β phospho-isoform and fasting plasma FFA (FIG. 3B), whereas in DM2 subjects the expression of this phospho-isoform did not correlate with FFA but instead correlated inversely with fasting plasma glucose (FIG. 3A). This is interesting, because a positive correlation of uncoupling protein 3 mRNA levels in muscle with circulating levels of FFA in non-diabetic subjects in the fasting state (23) seems to be absent in DM2 subjects (24) and replaced by an association to hyperglycemia (25), exactly as observed with the down-regulated ATPsyn-β phospho-isoform.

In summary, using proteome analysis the present inventors found that fifteen proteins surprisingly were up- or down regulated in muscle of subjects with DM2. Eleven of these proteins were positively identified by mass spectrometry. The proteins can be used as protein markers of DM2 in skeletal muscle in the post absorptive state. The type VI collagen isoforms have not been disclosed as being up-regulated in skeletal muscular tissue in diabetics, and the rest of these eleven proteins have not previously been directly associated with DM2.

Most surprisingly, the present inventors demonstrated that the catalytic β-subunit of $F_1$-ATP synthase is phosphorylated. In addition, the present inventors found expression of a β-subunit phospho-isoform in diabetic muscle to be reduced and to correlate inversely with plasma glucose levels. These data show a role for phosphorylation of ATPsyn-β in the regulation of ATP synthesis, and indicate that alterations in the regulation of this protein contribute to pathogenesis of DM2.

TABLE 1

Clinical characteristics

|  | Control | DM2 | P |
|---|---|---|---|
| n | 6 | 9 |  |
| Age (years) | 46.1 ± 1.5 | 44.8 ± 1.5 | ns |
| Body mass index (kg/m$^2$) | 25.7 ± 1.2 | 33.3 ± 1.9 | 0.01 |
| Male/female | 3/3 | 5/4 | ns |
| Fasting glucose (mmol/l) | 5.3 ± 0.1 | 8.5 ± 0.7 | 0.002 |
| Fasting FFA (mmol/l) | 0.28 ± 0.04 | 0.44 ± 0.08 | ns |
| Fasting insulin (pmol/l) | 37 ± 11 | 93 ± 12 | 0.005 |
| Fasting C-peptide (pmol/l) | 575 ± 120 | 1195 ± 93 | 0.001 |

Clinical characteristics of type 2 diabetic (DM2) and control subjects. Data represent mean ± s.e.m.
P values are calculated by Student's t-test;
ns, not significant.
Male/female ratio was tested by Chi-square test.

TABLE 3

Protein markers of type 2 diabetes not identified by MS

| Match No | Expression (% IOD) | | ~pI § | ~mW (kDa) § |
|---|---|---|---|---|
| | DM2 | Control | | |
| 199 | 0.025 ± 0.015 | 0.067 ± 0.032** | ~5.2 | ~45 |
| 303 | 0.154 ± 0.049 | 0.098 ± 0.047* | ~5.6 | ~55 |
| 391 | 0.028 ± 0.028 | 0.072 ± 0.046* | ~5.0 | ~25 |
| 511 | 0.052 ± 0.020 | 0.023 ± 0.013** | ~4.9 | ~65 |

Expression levels presented as percentage integrated optical density (% IOD), mean ± SD.
§, approximate values predicted from location on the 2 dimensional gel.
**$P < 0.01$;
*$P < 0.05$.
The expression level % IOD is given as determined using IPG gels covering the pH range from nominally 4 to 7. The actual values may be different if the gel system used is different to that used here.

Testing for Up- or Down-Regulation of the Proteins

A small percutaneous needle biopsy is collected from the vastus lateralis muscle and expelled into a hypotonic solution (to burst the cells and mitochondria). This solution contains protease, kinase and phosphorylase inhibitors. The sample is shaken for 15 minutes to release the proteins and then 100 μl is applied to the appropriate wells of appropriately prepared ELISA microtitre plates.

The microtitre plates have been coated with antibodies (either monoclonal or polyclonal, one in each row (except for the standards actin and rubisco)) which specifically recognise ATPsynthase, the phosphorylated form of ATP synthase, and some or all of the other proteins identified in table 2. Antibodies against other proteins, for example glycogen synthase can also be included. In addition a positive control is included (for example actin), and a negative control (i.e. a protein that should not be recognised like the plant protein rubisco) is included to make sure that the immunological reactions are working correctly. Furthermore, the plate contains standard curves for the various proteins in question as illustrated below. These standard curves can be made using recombinant proteins, modified or cleaved appropriately.

TABLE 2

Protein markers of type 2 diabetes identified by MALDI TOF MS analysis

| Spot no. | Protein | Database acc. no. | Theoretical pI/mW | Sequence Coverage | Matched peptides | Control group % IOD ± SEM | Diabetic group % IOD ± SEM |
|---|---|---|---|---|---|---|---|
| 180 | ATP synthase β-subunit | P06576 | 5.0/52 | 56% | 19 | 0.56 ± 0.05 | 0.41 ± 0.03 ** |
| 10 | Collagen alpha 1 (VI) chain | P12109 | 5.3/110 | 10% | 10 | 0.06 ± 0.01 | 0.09 ± 0.01 * |
| 11 | Collagen alpha 1 (VI) chain | P12109 | 5.3/110 | 5% | 5 | 0.04 ± 0.00 | 0.06 ± 0.01 ** |
| 407 | Collagen alpha 1 (VI) chain | P12109 | 5.3/110 | 6% | 6 | 0.05 ± 0.01 | 0.08 ± 0.01 * |
| 520 | Collagen alpha 1 (VI) chain | P12109 | 5.3/110 | 6% | 5 | 0.06 ± 0.01 | 0.09 ± 0.01 * |
| 541 | Creatine kinase B | P12277 | 5.3/43 | 42% | 12 | 0.32 ± 0.04 | 0.20 ± 0.02 * |
| 375 | Glucose regulated protein 78 | P11021 | 4.9/78 | 28% | 12 | 0.06 ± 0.01 | 0.08 ± 0.01 * |
| 81 | Heat shock protein 90 beta | P08238 | 5.0/84 | 15% | 11 | 0.03 ± 0.01 | 0.05 ± 0.00 * |
| 295 | Myosin regulatory light chain 2 (A) | P10916 | 4.9/19 | 58% | 9 | 1.26 ± 0.10 | 0.92 ± 0.10 * |
| 445 | Myosin regulatory light chain 2 (B) | AAK52797 | 4.9/19 | 52% | 7 | 0.30 ± 0.08 | 0.69 ± 0.12 * |
| 456 | Phosphoglucomutase 1 | P36871 | 6.2/62 | 25% | 12 | 0.14 ± 0.04 | 0.28 ± 0.04 * |

Identified protein markers of type 2 diabetes in skeletal muscle are given with their database accession numbers, theoretical molecular weight (mW) and pI.
The expression levels of these protein markers are given as mean ± SEM of the percentage integrated optical density (% IOD) of proteins.
* $P < 0.05$ vs. control;
** $P < 0.01$ vs. control.

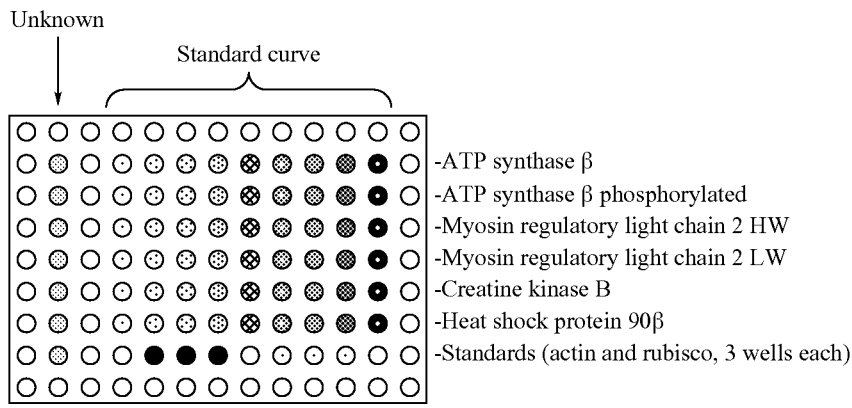

The microtitre plates are then left for 1 hr at 4° C., and then they are washed, developed and read in an ELISA plate reader. Certain readers are also capable of calculating the actual amount of the specific protein in the unknown sample with reference to the standard curve. The plate is rejected if actin does not stain or if rubisco does.

Each protein is known to have an average value and maximum and minimum tolerance limits (corresponding to the usual range seen in healthy individuals). When the protein exceeds these limits, the person can be considered as developing a particular disease related to diabetes type 2. Positive indications from 2 or more of the diagnostic markers are much more significant than from only one. For example, high creatine kinase B results are seen in patients that have recently experienced ischaemia and so this marker—on its own—is not sufficient to indicate diabetes type 2.

There are of course many other formats and procedures that are known to one skilled in the art which could be used to reach essentially identical diagnostic conclusions. The data obtained herewith can also be combined with other data relevant to the development of diabetes, for example serum glucose, or free fatty acid levels in order to increase the reliability of specificity of the diagnosis or prognosis.

REFERENCES

1. Beck-Nielsen, H. Mechanisms of insulin resistance in non-oxidative glucose metabolism: The role of glycogen synthase. *J. Basic Clin. Physiol. Pharmacol.* 9, 255-279 (1998).
2. Kelley, D. E., Mandarino, L. J. Fuel selection in human skeletal muscle in insulin resistance. A reexamination. *Diabetes* 49, 677-683 (2000).
3. Gebhart, S., Shoffner, J. M., Koontz, D., Kaufmann, A. & Wallace, D. Insulin resistance associated with maternally inherited diabetes and deafness. *Metabolism.* 45, 526-531 (1996).
4. Wallace, D. C. Mitochondrial diseases in man and mouse. *Science* 283, 1482-1488 (1999).
5. Pandey, P., Mann, M. Proteomics to study genes and genomes. *Nature* 405, 837-846 (2000).
6. Hickson, R. C., Heusner, W. W. & Van Huss, W. D. Skeletal muscle enzyme alterations after sprint and endurance training. *J. Appl. Physiol.* 40, 868-871 (1976).
7. Lillioja, S. et al. Skeletal muscle capillary density, and fiber type are possible determinants of in vivo resistance in man. *J. Gun. Invest.* 80, 415-424 (1987).
8. Pearl, H. P., Prodromou, C. Structure and in vivo function of Hsp90. *Curr. Opin. Struct. Biol.* 10, 46-51 (2000).
9. Nishizawa, J. et al. Reactive oxygen species play an important role in the activation of heat shock factor 1 in ischemic-reperfused heart. *Circulation* 99, 934-941(2000).
10. Nishikawa, T. et al. Normalizing mitochondrial superoxide production blocks three pathways of hyperglycaemic damage. *Nature* 404, 787-790 (2000).
11. Sato, S., Fujita, N. & Tsuruo, T. Modulation of Akt kinase activity by binding to Hsp90. *Proc. Natl. Acad. Sci. USA* 97, 10832-10837 (2000).
12. Garcia-Cardena, G. et al. Dynamic activation of endothelial nitric oxide synthase by Hsp90. *Nature* 392, 821-824 (1998).
13. Fryer, L. G. D. et al. Activation of glucose transport by AMP-activated protein kinase via stimulation of nitric oxide synthase. *Diabetes* 49, 1978-1985 (2000).
14. Poetter, K. et al. Mutations in either the essential or regulatory light chains of myosin are associated with a rare myopathy in human heart and skeletal muscle. *Nature Genetics* 13, 63-69 (1996).
15. Apple, F. S. Tissue specificity of cardiac troponin I, cardiac troponin T and creatine kinase-MB. *Clin. Chim. Acta.* 284, 151-159 (1999).
16. Apple, F. S. & Tesch, P. A. CK and LD isoenzymes in human single muscle fibres in trained athletes. *J. Appl. Physiol.* 66, 2717-2720 (1989).
17. Wallimann, T. et al. Some new aspects of creatine kinase (CK): compartmentation, structure, function and regulation for cellular and mitochondrial bioenergetics and physiology. *Biofactors* 8, 229-234 (1998).
18. Winder, W. W. & Hardie, D. G. AMP-activated protein kinase, a metabolic master switch: possible roles in Type 2 diabetes. *Am. J. Physiol. Endocrinol. Metab.* 277, E1-E10 (1999).
19. Boyer, P. D. Catalytic site forms and controls in ATP synthase catalysis. *Biochim. Biophys. Acta* 1458, 252-262 (2000).
20. Groth, G. Mills, D. A., Christiansen, E. Richter, M. L. & Huchzermeyer, B. Characterization of a phosphate binding domain on the α-subunit of chloroplast ATP synthase using the photoaffinity phosphate analogue 4-azido-2-nitrophenyl phosphate. *Biochemistry* 39, 13781-13787 (2000).
21. Wu, Z. et al. Mechanism controlling mitochondrial biogenesis and respiration through the thermogenic coactivator PGC-I. *Cell* 98 115-124 (1999).

22. Gonzalez, B, Hernando, R. & Manso, R. Stress proteins of 70 kDa in chronically exercised skeletal muscle. *Pflugers Arch—Eur. J. Physiol.* 440, 42-49 (2000).
23. Boss, O., Hagen, T. & Lowell, B. B. Uncoupling proteins 2 and 3. Potential regulators of mitochondrial energy metabolism. *Diabetes* 49, 143-156 (2000).
24. Shrauwen, P. et al. The effect of weight reduction on skeletal muscle UCP2 and UCP3 mRNA expression and UCP3 protein content in Type II diabetic subjects. *Diabetologia* 43, 1408-1416 (2000).
25. Bao, S. et al. Expression of mRNAs encoding uncoupling proteins in human skeletal muscle. Effects of obesity and diabetes. *Diabetes* 47, 1935-1940 (1998).
26. Højlund, K. et al. Reference intervals for glucose, n-cell polypeptides, and counter-regulatory factors during prolonged fasting. *Am. S. Physiol. Endocrinol. Metab.* 280, E50-E58 (2001).
27. Fey, S. J. et al. Proteome analysis of *Saccharomyces cerevisiae*: a methodological outline. *Electrophoresis* 8, 1361-1372 (1997).
28. Jensen, O. N., Larsen, M. R., Roepstorff, P., Mass spectrometric identification and microcharacterization of proteins from electrophoretic gels: strategies and applications. *Proteins* 2, 74-89 (1998).
29. Fey, S. J., Nawrocki, A., Larsen, M. R., Gorg, A., Roepstorff, P., Skews, G. N., Williams, R. & Larsen, P. M. (1997) *Electrophoresis* 8, 1361-72.
30. Hemmer, W., Skarli, M. Perriard, J. C. & Wallimann, T. (1993) FEBS letters 327, 35-40.
31. Manning, D. R. & Stull, S. (1982) Am. J. Physiol. 242, C234-241.
32. Menz, R. I., Walker, J. E. & Leslie, A. G. W. (2001) Cell 106, 331-341.

---

The invention claimed is:

1. A method for indicating type 2 diabetes in a human, the method comprising determining the, activity, concentration and/or level of expression of at least two marker proteins in a biological sample from the human, and comparing the, activity, concentration and/or level of expression of said proteins with the, activity, concentration and/or level of expression of said proteins in a biological sample from at least one normal human, wherein the sample is selected from the group consisting of urine, blood, lymphatic fluids and skeletal muscle tissues, and wherein the marker proteins are selected from the group consisting of:

(a) ATP synthase beta subunit or phosphorylated ATP synthase beta subunit isoforms;
(b) phosphoglucomutase 1;
(c) heat shock protein 90 beta;
(d) creatine kinase B subunit;
(e) myosin regulatory light chain 2;
(f) collagen alpha1 (VI) chain; and
(g) 78 kDa glucose-regulated protein.

* * * * *